(12) United States Patent
Abe et al.

(10) Patent No.: US 11,896,419 B2
(45) Date of Patent: Feb. 13, 2024

(54) X-RAY DIAGNOSTIC APPARATUS

(71) Applicant: CANON MEDICAL SYSTEMS CORPORATION, Tochigi (JP)

(72) Inventors: Shingo Abe, Nasushiobara (JP); Kunitoshi Matsumoto, Nasushiobara (JP)

(73) Assignee: CANON MEDICAL SYSTEMS CORPORATION, Tochigi (JP)

( * ) Notice: Subject to any disclaimer, the term of this patent is extended or adjusted under 35 U.S.C. 154(b) by 136 days.

(21) Appl. No.: 17/643,939

(22) Filed: Dec. 13, 2021

(65) Prior Publication Data
US 2022/0183648 A1 Jun. 16, 2022

(30) Foreign Application Priority Data
Dec. 14, 2020 (JP) .................................. 2020-206512

(51) Int. Cl.
*A61B 6/00* (2006.01)

(52) U.S. Cl.
CPC .............. *A61B 6/541* (2013.01); *A61B 6/467* (2013.01); *A61B 6/481* (2013.01); *A61B 6/482* (2013.01); *A61B 6/542* (2013.01)

(58) Field of Classification Search
CPC ......... A61B 6/541; A61B 6/467; A61B 6/481; A61B 6/482; A61B 6/542; A61B 6/4441; A61B 6/5264; A61B 8/0841; A61B 6/40; A61B 6/4035; A61B 6/42; A61B 6/54
See application file for complete search history.

(56) References Cited

U.S. PATENT DOCUMENTS

2018/0368798 A1* 12/2018 Meyer .................... A61B 6/463

FOREIGN PATENT DOCUMENTS

JP 2017-131310 A 8/2017

\* cited by examiner

*Primary Examiner* — Courtney D Thomas
(74) *Attorney, Agent, or Firm* — Oblon, McClelland, Maier & Neustadt, L.L.P.

(57) ABSTRACT

An X-ray diagnostic apparatus of an embodiment includes an input interface, and processing circuitry. The input interface accepts an input operation performed by an operator. The processing circuitry identifies a period in which periodic movement is small in an X-ray irradiation area. The processing circuitry determines irradiation start timing of an X-ray according to the period. The processing circuitry controls to perform X-ray irradiation of a relatively high dose in the determined irradiation start timing on condition that the input operation is being continued.

24 Claims, 12 Drawing Sheets

X-RAY DIAGNOSTIC APPARATUS

CROSS-REFERENCE TO RELATED APPLICATIONS

This application is based upon and claims the benefit of priority from Japanese Patent Application No. 2020-206512, filed on Dec. 14, 2020; the entire contents of which are incorporated herein by reference.

FIELD

Embodiments disclosed in the present application and drawings relate to an X-ray diagnostic apparatus.

BACKGROUND

In vascular interventional treatments, an indwelling treatment in which a device for treatment inserted in a blood vessel is brought accurately to a position of a treatment site, and the device is left inside the body, or a dilatation treatment in which a narrowing area is mechanically dilated by expanding the device is performed. In this treatment, it is necessary to determine a position at which the treatment is performed, and to confirm completion of the treatment, and the doctor normally refers to radiographic images that are generated and displayed in real time by an X-ray diagnostic apparatus, to perform the treatment and to confirm completion thereof. For example, as markers to show a position of a balloon or a stent, a radiopaque metal part is attached to a device at two positions (one position in some cases). The doctor checks the marker in the radiographic image that is displayed on a monitor, to determine a position at which the treatment is performed. Furthermore, the doctor checks the device rendered in the radiographic image, and confirms completion of the treatment.

However, in the vascular interventional treatment of an organ that makes pulsatile movement, such as heart, the position of the device moves in the radiographic image. Therefore, the visibility of the device is deteriorated, and determination of a position at which the treatment is performed for a treatment site and to confirm completion of the treatment is a task requiring an advanced skill for the doctor.

To deal with this, a technique of displaying moving images in which a device virtually looks unmoving by tracking the markers at two points rendered in radiographic images sequentially generated, and by subjecting the radiographic images to deformation processing and position adjustment processing such that positions of the markers at two points in the respective radiographic images coincide with positions in past images has been known. Moreover, a technique of highlighting the device in high contrast by subjecting plural frames of images that have been corrected such that the positions of the two markers coincide with one another to, for example, signal averaging in a post process has also been known.

DETAILED DESCRIPTION

An X-ray diagnostic apparatus according to an embodiment includes an input interface and processing circuitry. The input interface is configured to accept an input operation performed by an operator. The processing circuitry is configured to identify a period in which periodic movement is small in an X-ray irradiation area. The processing circuitry is configured to determine X-ray irradiation start timing according to the period. The processing circuitry is configured to control to irradiate an X-ray of relatively high dose in the determined irradiation start timing on condition that the input operation continues.

Hereinafter, embodiments of the X-ray diagnostic apparatus will be explained in detail with reference to the drawings. The X-ray diagnostic apparatus according to the present application is not limited to the embodiments described below. Moreover, the embodiments can be combined with another embodiment or a conventional technique within a range not causing contradiction in processing. Furthermore, in the following explanation, common reference symbols are assigned to identical components, and duplicated explanation will be omitted.

First Embodiment

Figure 1:
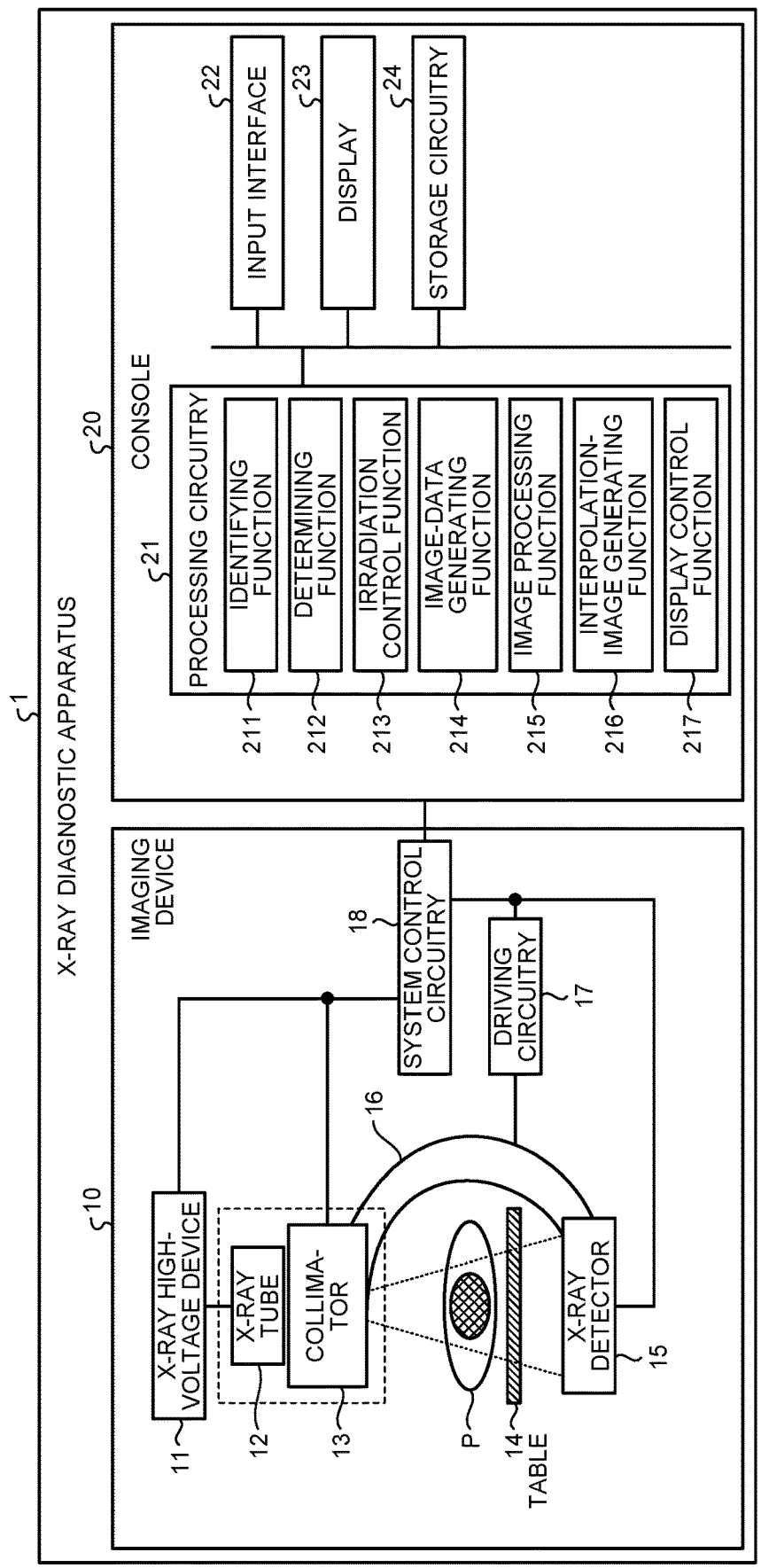
FIG. 1 is a block diagram illustrating an example of a configuration of an X-ray diagnostic apparatus according to a first embodiment.

A configuration of an X-ray diagnostic apparatus according to a first embodiment will be explained. FIG. 1 is a block diagram illustrating an example of a configuration of an X-ray diagnostic apparatus 1 according to the first embodiment. As illustrated in FIG. 1, the X-ray diagnostic apparatus 1 includes an imaging device 10 and a console 20, and are connected through system control circuitry 18. The imaging device 10 includes an X-ray high-voltage device 11, an X-ray tube 12, a collimator 13, a table 14, an X-ray detector 15, a C-arm 16, driving circuitry 17, and system control circuitry 18. The console 20 includes processing circuitry 21, an input interface 22, a display 23, and storage circuitry 24.

The X-ray high-voltage device 11 supplies a high voltage to the X-ray tube 12 under control of the system control circuitry 18. For example, the X-ray high-voltage device 11 has an electric circuit, such as a transformer and a rectifier, and has a high-voltage generator that generates a high voltage to be applied to the X-ray tube 12, and an X-ray control device that controls an X-ray tube voltage, a X-ray tube current, and irradiation time according to an X-ray irradiated by the X-ray tube 12. The high-voltage generator may be of transformer type, or may be of inverter type.

The X-ray tube 12 is a vacuum tube having a cathode (filament) that generates thermions, and an anode (target) that receives collision of thermions to generate X-rays. The X-ray tube 12 generates X-rays by accelerating the thermions emitted from the cathode and making them collide with the anode by using a high voltage supplied from the X-ray high-voltage device 11.

The collimator 13 includes an X-ray aperture that narrows an irradiation range of X-rays generated by the X-ray tube 12, and a filter to adjust the X-ray emitted from the X-ray tube 12.

The X-ray aperture in the collimator 13 includes, for example, four pieces of slidable aperture blades. The X-ray aperture slides the aperture blades, and thereby limits an X-ray generated by the X-ray tube 12 to be irradiated to a subject P. The aperture blade is a plate-shaped member made from lead or the like, and is arranged near an X-ray irradiation window of the X-ray tube 12 to adjust an irradiation range of an X-ray.

The filter in the collimator 13 is provided to reduce an exposure dose of the subject P and to improve the image quality of X-ray image data, and changes a quality of X-ray passing therethrough by its material and thickness to reduce low energy components easy to be absorbed by the subject P.

For example, the collimator 13 includes a driving mechanism of a motor, an actuator, and the like, and controls irradiation of an X-ray by actuating the driving mechanism under control of the system control circuitry 18. For example, the collimator 13 controls an irradiation range of an X-ray to be irradiated to the subject P by adjusting an aperture of the aperture blades of the X-ray aperture, by applying a driving voltage to the driving mechanism according to a control signal received from the system control circuitry 18.

The table 14 is a bed on which the subject P is laid, and is arranged on a bed unit not illustrated. The subject P is not included in the X-ray diagnostic apparatus 1. For example, the bed unit includes a driving mechanism, such as a motor and an actuator, and controls movement and tilting of the table 14 by actuating the driving mechanism under control of the system control circuitry 18.

The X-ray detector 15 is an X-ray flat panel detector (FPD) having detecting devices that are arranged, for example, in a matrix. The X-ray detector 15 detects an X-ray that has been irradiated from the X-ray tube 12, and has passed through the subject P, and outputs a detection signal corresponding to a detected X-ray amount to an image-data generating function 214. The X-ray detector 15 may be an indirect conversion detector including a scintillator array, and an optical sensor array, or may be a direct conversion detector including a semiconductor device that converts an incident X-ray into an electrical signal. Moreover, it may be an X-ray detector that is capable of non-destructive and multiple readouts described later.

The C-arm 16 holds the X-ray tube 12 and the collimator 13, and the X-ray detector 15, so as to oppose to each other sandwiching the subject P. For example, the C-arm 16 includes a driving mechanism, such as a motor and an actuator, and rotates and moves through the driving circuitry 17 under control of the system control circuitry 18. Although a case in which the X-ray diagnostic apparatus 1 is a single plane type is explained as an example in FIG. 1, embodiments are not limited thereto, and it may be a biplane type.

The driving circuitry 17 is implemented by, for example, a processor. The driving circuitry 17 controls the C-arm 16 according to a control signal accepted by the system control circuitry 18, and rotates and moves the X-ray tube 12, the collimator 13, and the X-ray detector 15 with respect to the subject P. The driving circuitry 17 may be included in the system control circuitry 18.

The system control circuitry 18 is implemented by, for example, a processor. The system control circuitry 18 controls overall operations of the imaging device 10 by controlling the X-ray high-voltage device 11, the X-ray tube 12, the collimator 13, the X-ray detector 15, the bed unit, and the driving circuitry 17 under control of an irradiation control function 213. For example, the system control circuitry 18 controls the C-arm 16 through the driving circuitry 17, and thereby rotates and moves the X-ray tube 12, the collimator 13, and the X-ray detector 15 with respect to the subject P. Furthermore, the system control circuitry 18 controls movement of the bed unit, and thereby moves or tilts the table 14. Moreover, the system control circuitry 18 controls the X-ray high-voltage device 11 according to a control signal accepted from the irradiation control function 213, to irradiate X-rays to the subject P.

Moreover, the system control circuitry 18 controls the X-ray high-voltage device 11 to adjust a voltage to be supplied to the X-ray tube 12. The X-ray high-voltage device 11 thereby controls an X-ray dose to be irradiated to the subject P or ON/OFF. Moreover, the system control circuitry 18 outputs a detection signal detected by the X-ray detector 15 to the storage circuitry 24 to temporarily store it.

For example, the system control circuitry 18 controls movement of the collimator 13 to adjust an aperture of the aperture blades of the X-ray aperture, and thereby controls an irradiation range of an X-ray to be irradiated to the subject P. Furthermore, the system control circuitry 18 controls movement of the collimator 13 to adjust a position of the filter, and thereby controls a distribution of a dose of an X-ray.

The processing circuitry 21 controls overall operation of the X-ray diagnostic apparatus 1 by performing identifying function 211, a determining function 212, the irradiation control function 213, the image-data generating function 214, an image processing function 215, an interpolation-image generating function 216, and a display control function 217. Specifically, the processing circuitry 21 controls the system control circuitry 18 and the console 20 by executing programs corresponding to the respective functions from the storage circuitry 24. Furthermore, the processing circuitry 21 controls overall operation of the X-ray diagnostic apparatus 1 by controlling the system control circuitry 18 and the imaging device 10.

The identifying function 211 is one example of an identifying unit. The determining function 212 is one example of a determining unit. Moreover, the irradiation control function 213 is one example of an irradiation control unit. The image-data generating function 214 is one example of an image generating unit. The image processing function 215 is one example of an image processing unit. Furthermore, the interpolation-image generating function 216 is one example of an interpolation-image generating unit. The display control function 217 is one example of a display control unit.

The identifying function 211 identifies a period in which the number of periodic movement is small in an X-ray irradiation range. Specifically, the identifying function 211 reads an amount of movement of respective positions (coordinates) in an X-ray image, and a cycle of movement based on the amount of movement calculated by the image processing function 215 based on the X-ray image generated by the image processing function 215, from the storage circuitry 24. The identifying function 211 identifies in what timing (phase) a period in which variation caused by heart beat is small appears next in an X-ray irradiation area of the subject P based on the amount of movement and the cycle of movement calculated by the image processing function 215. The identifying function 211 stores a processing result in the storage circuitry 24. The processing performed by the identifying function 211, the image-data generating function 214, and the image processing function 215 will be described in detail later.

The determining function 212 determines an X-ray condition relating to X-ray irradiation in the imaging device 10. The X-ray condition in the present embodiment is, for example, a condition relating to an X-ray to be irradiated by the X-ray tube 12 and the collimator 13, and includes a pulse width, a X-ray tube voltage, a X-ray tube current, a focal spot size, a radiation quality filter, a dose, and the like. Specifically, the determining function 212 determines the X-ray condition according to length of the period in which the number of periodic movement is small identified by the identifying function 211. Moreover, for example, the determining function 212 determines the X-ray condition according to a preset input to the input interface 22 by an operator. The X-ray condition determined by the determining function 212 is store in the storage circuitry 24. The X-ray condition stored in the storage circuitry 24 is used for X-ray irradiation control performed by the irradiation control function 213 described later. The processing performed by the determining function 212 will be described in detail later.

The irradiation control function 213 controls the system control circuitry 18, and thereby controls X-ray irradiation in the imaging device 10. Specifically, the irradiation control function 213 determines timing in which an irradiation control signal of an X-ray is output based on the next timing of the period in which the number of periodic movement is small identified by the identifying function 211, and delay time that is necessary until an X-ray is actually irradiated from when the irradiation control signal of an X-ray is output. Furthermore, the irradiation control function 213 controls such that X-ray irradiation is performed based on the X-ray condition determined by the determining function 212. The processing performed by the irradiation control function 213 will be described in detail later.

The image-data generating function 214 generates X-ray image data by using a detection signal detected by the X-ray detector 15, and stores the generated X-ray image data in the storage circuitry 24. For example, the image-data generating function 214 subjects the detection signal detected by the X-ray detector 15 to current voltage conversion, analog-to-digital (A/D) conversion, or parallel-serial conversion, to generate X-ray image data.

The image-data generating function 214 performs various kinds of image processing with respect to the X-ray image data stored in the storage circuitry 24. For example, the image processing function 215 performs noise degradation processing with respect to the X-ray image data. Moreover, the image processing function 215 performs degradation processing with respect to the X-ray image data, to generate an X-ray image having a quality equivalent to other X-ray images. A processing result of the image processing function 215 is stored in the storage circuitry 24.

Furthermore, the image processing function 215 calculates an amount of movement and a cycle of movement an X-ray image. Specifically, the image processing function 215 calculates an amount of movement in each position in an X-ray image by various kinds of image processing, to store in the storage circuitry 24. Furthermore, the image processing function 215 calculates a cycle of movement based on the calculated amount of movement, to store in the storage circuitry 24. The processing performed by the image processing function 215 will be described in detail later.

The interpolation-image generating function 216 generates interpolation images for X-ray image data constituted of plural frames and X-ray images stored in the storage circuitry 24 to interpolate therebetween. For example, the interpolation-image generating function 216 generates an interpolation image to interpolate between the last frame among plural frames of X-ray image that have been acquired to identify a period in which periodic movement of a subject to be observed by the identifying function 211 and an X-ray image that is generated by irradiating an X-ray at a relatively high dose. The interpolation image generated by the interpolation-image generating function 216 is stored in the storage circuitry 24. The processing performed by the interpolation-image generating function 216 will be described in detail later.

The display control function 217 causes the display 23 to display a graphical user interface (GUI) or an X-ray image. For example, the display control function 217 reads an X-ray image from the storage circuitry 24 in accordance with an operation made through the input interface 22, to display it on the display 23. Moreover, the display control function 217 controls transmission and reception of data with an external device through a network not illustrated in FIG. 1.

The input interface 22 accepts various kinds of input operations from an operator, and converts the accepted input operation into an electrical signal, to output to the processing circuitry 21. For example, the input interface 22 is implemented by a mouse, a keyboard, a trackball, a switch, a button, a joystick, a touch pad to make an input operation by touching an operating surface, a touch screen in which a display screen and a touch pad are integrated, a non-contact input circuit using an optical sensor, a sound input circuit, and the like. The input interface 22 may be constituted of a tablet terminal that can communicate with the device main unit by wireless communication, or the like. Furthermore, the input interface 22 is not limited to ones having physical operating parts, such as a mouse and a keyboard. For example, a processing circuit of an electrical signal that receives an electrical signal corresponding to an input operation from an external input device provided separately from the device, and that outputs this electrical signal to the processing circuitry 21 is also included in examples of the input interface 22.

The display 23 displays various kinds of information. For example, the display 23 displays a GUI to accept an instruction from an operator, or various kinds of X-ray images stored in the storage circuitry 24 by a control of the display control function 217. Moreover, the display 23 displays a processing result by the processing circuitry 21. For example, the display 23 displays an X-ray image generated by the image processing function 215 by X-ray irradiation of a high dose. Furthermore, the display 23 displays various kinds of X-ray images stored in the storage circuitry 24, and displays image information so that a user can distinguish the type of the X-ray image.

The storage circuitry 24 is implemented by, for example, a semiconductor memory device, such as a random access memory (RAM) and a flash memory, a hard disk, an optical disk, or the like. The storage circuitry 24 temporarily stores a processing result by the processing circuitry 21. For example, the storage circuitry 24 accepts image data generated by the image-data generating function 214, and temporarily stores it. Moreover, the storage circuitry 24 stores various kinds of data and various kinds of programs that are used by the processing circuitry 21. Specifically, the storage circuitry 24 is connected to the processing circuitry 21, and stores data input from the processing circuitry 21, or reads data stored therein to output to the processing circuitry 21. The storage circuitry 24 may be implemented by a server group (cloud) that is connected with the X-ray diagnostic apparatus 1 through a network.

One example of the configuration of the X-ray diagnostic apparatus 1 according to the present embodiment has so far been explained. Based on the configuration, the X-ray diagnostic apparatus 1 enables to facilitate observation of a device in a vascular interventional treatment by the processing by the processing circuitry 21. Specifically, the X-ray diagnostic apparatus 1 identifies a period in which variation caused by heartbeat of the subject P is small in a region of interest, and determines the X-ray condition to be optimal according to the identified period, to perform X-ray irradiation. Thus, observation of a device in a region of interest, visibility of which is reduced by heartbeat of the heart or the like can be facilitated.

As described above, the X-ray diagnostic apparatus can show a position of a device by displaying an X-ray image in which a radiopaque metal that is attached at two points on the device as a marker is shown in a vascular interventional treatment. Furthermore, the X-ray diagnostic apparatus detects a marker pair of the device, and performs image processing by adding up respective images to perform positioning such that movement caused by heartbeat of the heart or the like is canceled, and thereby renders a state of the device, such as a stent, which is normally difficult to be observed, with one piece of image, enabling easy observation.

However, a method of facilitating observation of a device by detecting a marker pair cannot be performed all the time. For example, when a device on which the marker pair is attached is not positioned in a region of interest, the above method cannot be performed. Specifically, when a stent is moved using a catheter on which a marker pair is attached as a guide for stent indwelling, a position and a state of the stent is checked by using the marker pair attached to the catheter. Because the catheter that has been used as the guide for the stent becomes unnecessary after the stent is left, the operator pulls out the catheter from a body, and the catheter will not be present in a region of interest. Therefore, after the stent is left, because the catheter on which the marker pair is attached is not present in the region of interest, the X-ray diagnostic apparatus 1 cannot perform detection of the stent or positioning with respect to X-ray images to be generated, and the position and the state of the stent cannot be grasped.

Moreover, there is a case in which an image enabling easy observation of a device cannot be generated due to degradation of detection accuracy of the marker pair. For example, there is a case in which a background component, such as an organ and a bone, overlaps a marker in an X-ray image, to reduce the detection accuracy, or a case in which a contrast of a marker is lowered due to a speed of movement of a device in X-ray images, a thickness of a body of the subject, an X-ray condition, or the like, to make detection of the marker pair difficult. In another case, there is a case in which detection of the marker pair cannot be performed properly because an amount of position change per frame is large when a frame rate of the X-ray diagnostic apparatus is low with respect to movement of the marker pair, or when an X-ray image is enlarged and the field of view is narrow.

Accordingly, the X-ray diagnostic apparatus 1 according to the present embodiment identifies a period in which movement caused by heartbeat of the heart or the like in an X-ray irradiation area is small without using a parker pair, determines the X-ray condition according to the period, and performs X-ray irradiation at a relatively high dose (high-dose X-ray irradiation), and thereby generates an image that enables easy observation of the device.

Figure 2:
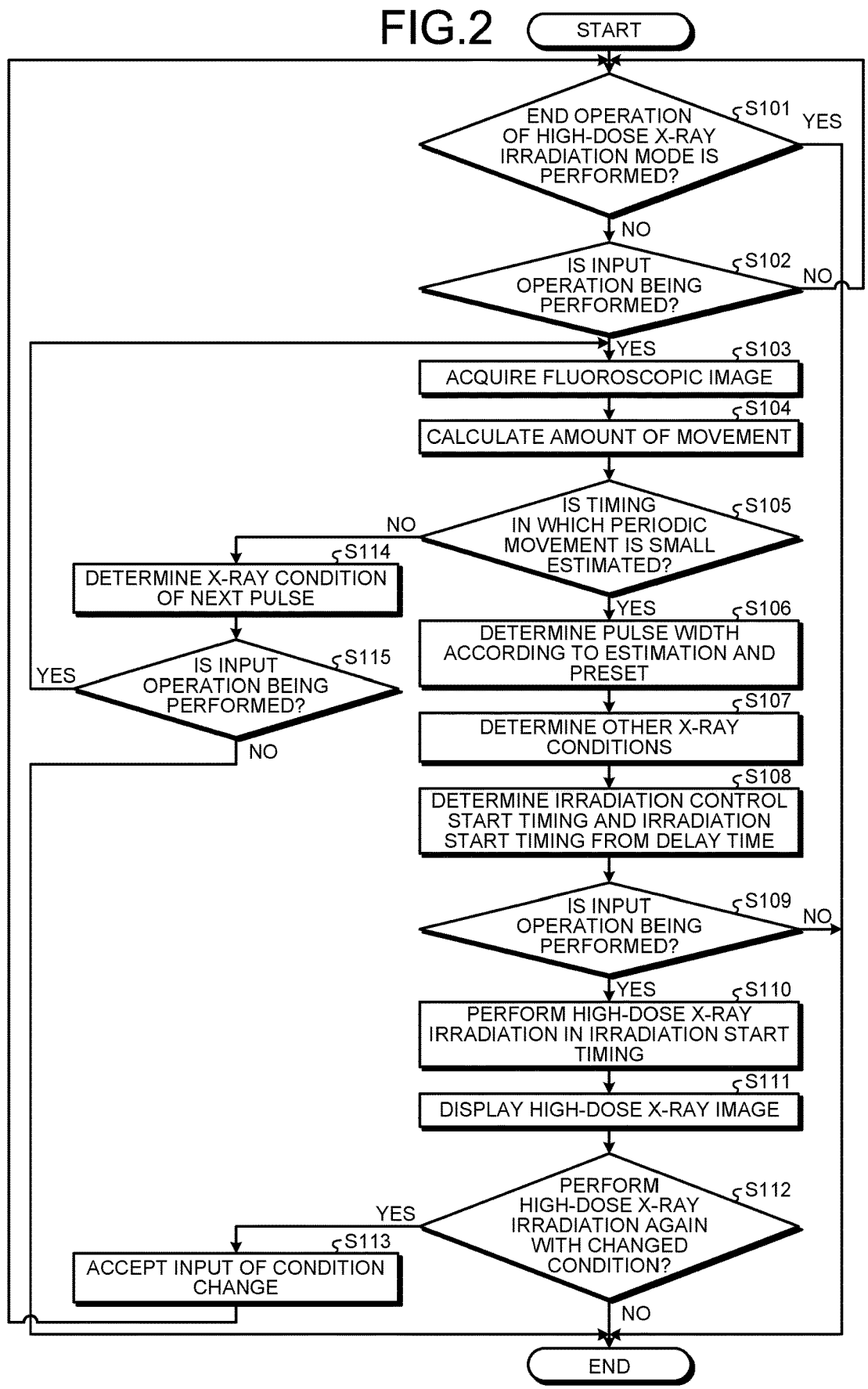
FIG. 2 is a flowchart illustrating a procedure of processing performed by the X-ray diagnostic apparatus according to the first embodiment.

A procedure of processing performed by the X-ray diagnostic apparatus 1 will be explained herein. FIG. 2 is a flowchart illustrating a procedure of the processing performed by the X-ray diagnostic apparatus 1 according to the first embodiment. Hereinafter, first an overview of respective steps in the flowchart will be explained, and then details of the processing in each step will be explained. Steps S101 to step S102 in FIG. 2 are implemented by the processing circuitry 21 reading and executing a program corresponding to the irradiation control function 213 from the storage circuitry 24. Moreover, step S103 is implemented by the processing circuitry 21 reading and executing a program corresponding to the irradiation control function 213 and the image-data generating function 214 from the storage circuitry 24. Furthermore, step S104 is implemented by reading and executing a program corresponding to the identifying function 211 and the image processing function 215 from the storage circuitry 24.

Furthermore, step S105 is implemented by the processing circuitry reading and executing a program corresponding to the identifying function 211 from the storage circuitry 24. Moreover, step S106 to step S107 are implemented by the processing circuitry 21 reading and executing a program corresponding to the determining function 212 from the storage circuitry 24. Furthermore, step S108 to step S110 are implemented by reading and executing a program corresponding to the irradiation control function 213 from the storage circuitry 24. Moreover, step S111 is implemented by the processing circuitry 21 reading and executing a program corresponding to the display control function 217, the image-data generating function 214, and the image processing function 215 from the storage circuitry 24. Furthermore, step S112 to step S113 are implemented by reading and executing a program corresponding to the irradiation control function 213 from the storage circuitry 24. Moreover, step S114 is implemented by the processing circuitry 21 reading and executing a program corresponding to the determining function 212 from the storage circuitry 24. Furthermore, step S115 is implemented by reading and executing a program corresponding to the irradiation control function 213 from the storage circuitry 24.

As illustrated in FIG. 2, in the X-ray diagnostic apparatus 1 according to the first embodiment, the processing circuitry 21 determines whether an end operation of a mode (high-dose X-ray irradiation mode) to perform a series of processing to perform high-dose X-ray irradiation has been performed (step S101). When the end operation has been performed (step S101: YES), the X-ray diagnostic apparatus 1 ends the processing. On the other hand, when the end operation of the high-dose X-ray irradiation mode has not been performed (step S101: NO), the input interface 22 accepts an input operation (for example, depression of a switch to irradiate an X-ray, or the like), and the processing circuitry 21 determines whether the input operation is being performed (step S102). When an input operation is not being performed (step S102: NO), the processing circuitry 21 returns to step S101.

On the other hand, when the input operation is being performed (step S101: YES), the processing circuitry 21 controls the imaging device 10 to perform fluoroscopy, to acquire a fluoroscopic image (step S103). The processing circuitry 21 calculates an amount of movement of respective positions and a cycle of movement of the fluoroscopic image (step S104). Furthermore, the processing circuitry 21 estimates next timing of a period in which periodic movement is small by using the calculated amount of movement and the cycle of movement, and determines whether the estimation has been done (step S105).

When the period in which periodic movement is small cannot be estimated (step S105: NO), an X-ray condition of a next pulse is determined (step S114). The processing circuitry 21 determines whether an input operation is being performed (step S115), and when the input operation is being performed (step S115: YES), acquires a fluoroscopic image. On the other hand, when the input operation is not being performed (step S115: NO), the processing circuitry 21 ends the processing.

At step S105, when the timing of the period in which periodic movement is small can be estimated (step S105: YES), the processing circuitry 21 determines a pulse width of an X-ray to be irradiated at step S110 described later according to the estimated period in which the periodic movement is small and a preset (step S106). Furthermore, the processing circuitry 21 determines X-ray conditions other than the pulse width (step S107).

Subsequently, the processing circuitry 21 determines irradiation control start timing and irradiation start timing based on the delay time necessary until an X-ray is actually irradiated from when the irradiation control signal of an X-ray is output (step S108).

The processing circuitry 21 determines whether an input operation is being performed (step S109), and when the input operation is not being performed (step S109: NO), ends the processing. On the other hand, when the input operation is being performed (step S109: YES), the processing circuitry 21 controls the imaging device 10 according to the irradiation start timing determined at step S108, and performs high-dose X-ray irradiation (step S110). Thereafter, the processing circuitry 21 generates an X-ray image of a relatively high dose by using a detection signal detected by irradiating an X-ray of a relatively high dose by the imaging device 10, and displays the generated X-ray image (high-dose X-ray image) on the display 23 (step S111).

Subsequently, the processing circuitry 21 determines whether an input to perform high-dose X-ray irradiation again, changing conditions has been accepted by the input interface (step S112). When the input to perform the high-dose X-ray irradiation with changed conditions has been accepted (step S112: YES), the processing circuitry 21 accepts an input of condition change (step S113). For example, the processing circuitry 21 accepts an input of a change of the X-ray condition including the pulse width. The processing circuitry 21 then returns to step S101 to perform the processing. On the other hand, when an input to perform high-dose X-ray irradiation with changed conditions has not been accepted (step S112: NO), the processing circuitry 21 ends the processing of the high-dose X-ray irradiation mode.

Figure 3:
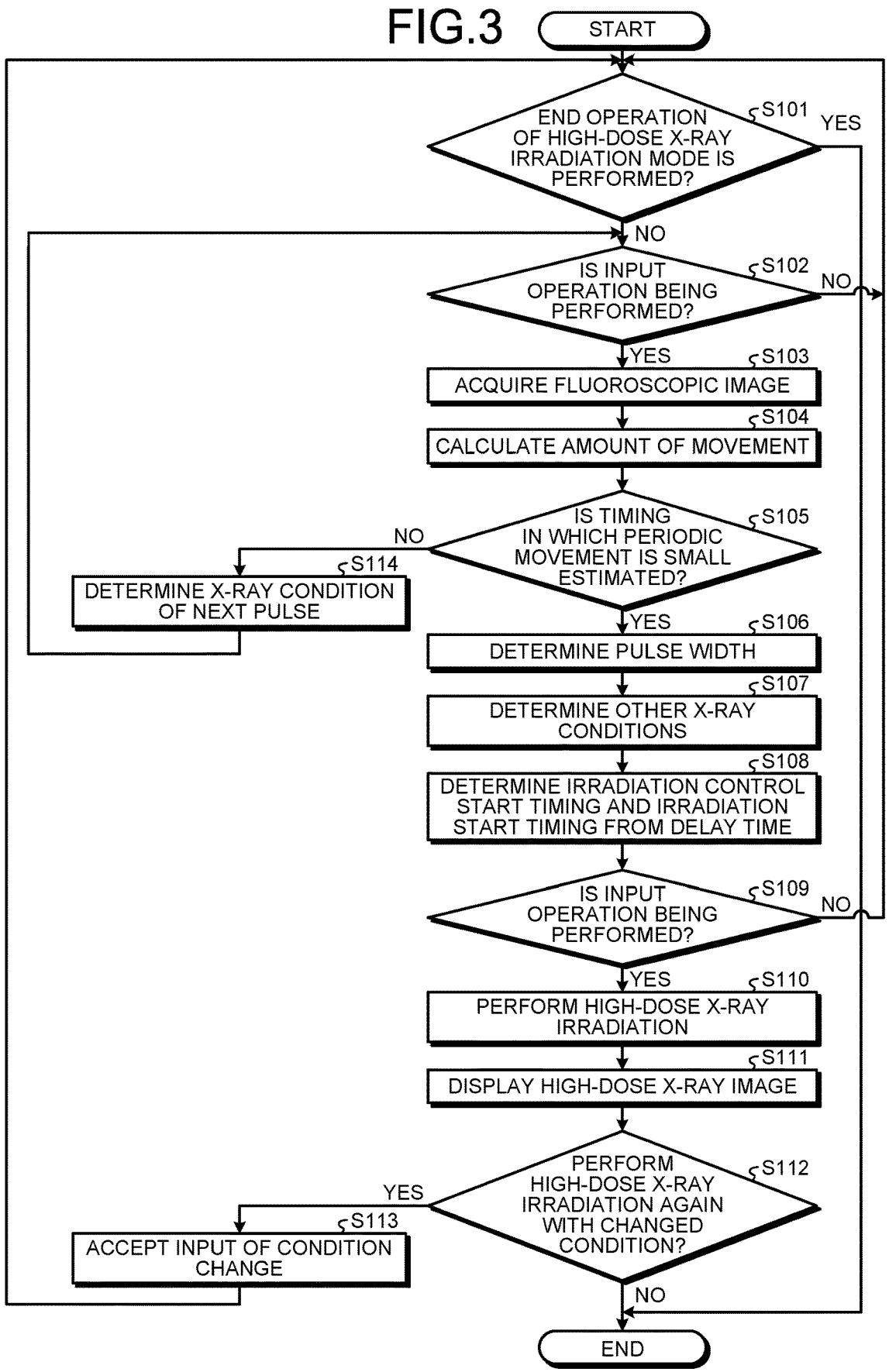
FIG. 3 is a flowchart illustrating a modification of the procedure of processing performed by the X-ray diagnostic apparatus according to the first embodiment.

In the procedure of the processing illustrated in FIG. 2, the example in which the processing is ended when an input operation is not being performed in determination whether an input operation is being performed by an operator (for example, step S109, or the like) has been explained. However, when an input operation is not being performed in the above determination, the processing flow may be returned to the start point. FIG. 3 is a flowchart illustrating a modification of the procedure of the processing performed by the X-ray diagnostic apparatus 1 according to the first embodiment. Compared with the flowchart illustrated in FIG. 2, FIG. 3 differs in processing after the determination at step S109, and in a point in which step S115 is not included. In the following, these points are mainly explained.

As illustrated in FIG. 3, in the X-ray diagnostic apparatus 1 according to the modification, processing is performed similarly to that in FIG. 2 at step S101 to step S108. In the determination at step S109, when an input operation is not being performed (step S109: NO), the processing circuitry 21 returns to step S101 to perform the processing. On the other hand, when the input operation is being performed (step S109: YES), the processing circuitry 21 performs high-dose X-ray irradiation similarly to FIG. 2 (step S110).

Moreover, in the X-ray diagnostic apparatus 1 according to the modification, when the X-ray condition of a next pulse is determined at step S114, it is returned to step S102 to perform the processing. In the X-ray diagnostic apparatus 1 according to a second modification, processing is performed similarly to FIG. 2 also at step S110 to step S113. According to the modification described above, for example, when a case in which an input operation cannot be continued occurs, end of processing according to an intention of an operator can be determined.

Hereinafter, details of the processing performed by the X-ray diagnostic apparatus 1 according to the first embodiment will be explained. In the first embodiment, as the processing to identify timing in which periodic movement is small, a case of identifying a period in which fluctuation caused by heartbeat is small by using a fluoroscopic image will be explained as an example.

The X-ray diagnostic apparatus 1 according to the first embodiment performs fluoroscopy when an operation by an operator continues, and identifies a period in which periodic movement caused by heartbeat of the heart is small at respective positions in collected fluoroscopic images. The X-ray diagnostic apparatus 1 determines timing to start the X-ray irradiation control (timing of outputting the irradiation control signal), and timing to perform X-ray irradiation according to the identified period (timing of actual irradiation), and performs X-ray irradiation at a relatively high dose. Thus, the X-ray diagnostic apparatus 1 suppresses deterioration of visibility of a device caused an influence of heartbeat of the heart, and displays an X-ray image in which the visibility of the device is improved. When the input operation to execute X-ray irradiation by the operator is stopped, the processing is stopped.

Input Interface

For the input interface 22 that accepts a continuous input operation by an operator, for example, an input interface that is operated by the operator himself/herself by pressing at desirable timing to control X-ray irradiation, such as a foot switch and a hand switch mounted on an ordinary X-ray diagnostic apparatus may be used. Moreover, for example, the input interface 22 may be a dedicated switch that is used only for a series of processing according to the present embodiment, to distinguish processing to perform a series of X-ray irradiation of the present embodiment and a series of processing to perform normal X-ray irradiation. Furthermore, an input operation of the present embodiment may be allocated to a function switch to which a function can be arbitrarily allocated by an operator.

The input interface 22 may include a switching switch to switch between a mode to perform normal X-ray irradiation in which the high-dose X-ray irradiation of the present embodiment is not performed (normal X-ray irradiation mode) and a mode in which the high-dose X-ray irradiation of the present embodiment is performed (the high-dose X-ray irradiation mode). Specifically, a function to perform X-ray irradiation in the high-dose X-ray irradiation mode may be allocated to a switch to which a function of performing normal X-ray irradiation in a normal X-ray irradiation mode is allocated when the high-dose X-ray irradiation mode is selected by the switching switch by the operator.

Moreover, the input interface 22 accepts an input of the X-ray condition relating to X-ray irradiation in advance. For example, before laying the subject on the table 14 of the X-ray diagnostic apparatus 1, the X-ray condition of body thickness of the subject and apparatus specification of the X-ray diagnostic apparatus 1 may be set by the operator in advance. Furthermore, in the present embodiment, the X-ray condition may be specified for both fluoroscopy and X-ray irradiation of a relatively high dose. Thus, after the high-dose X-ray irradiation mode is performed, the X-ray condition corresponding to variations of the subject can be determined within the range of the X-ray condition specified by the operator, to perform irradiation.

Continuation of Input Operation

As described above, the processing circuitry 21 performs a series of processing to perform the high-dose X-ray irradiation on condition that the input operation is being performed. That is, when the high-dose X-ray irradiation mode is selected, the operator can operate the X-ray diagnostic apparatus 1 from acquisition of a fluoroscopic image to execution of X-ray irradiation of a relatively high dose, and to display on the display only by continuing the input operation. For example, when the condition is continuous depression of the switch to irradiate an X-ray, only by performing the operation similar to the normal X-ray irradiation mode, a high-dose X-ray image can be displayed. That is, the number of times of instructing X-ray irradiation to the X-ray diagnostic apparatus by the operator during treatment is one, and a load on the operator can be reduced. Moreover, when the input operation is not continued, by ending the processing in the high-dose X-ray irradiation mode, unnecessary X-ray irradiation can be prevented, and radiation exposure can be reduced.

Collection of Fluoroscopic Images

As described above, at step S103, the processing circuitry 21 performs fluoroscopy in a period including plural heartbeats, to collect fluoroscopic images. Specifically, the irradiation control function 213 in the processing circuitry 21 outputs the irradiation control signal, to sequentially irradiate X-rays of a relatively low dose corresponding to fluoroscopy. The X-ray condition for fluoroscopy may be input in advance (preset) through the input interface 22, or may be determined by using an automatic brightness control (ABC). The ABC is a control in which a statistical value of a pixel value in a fluoroscopic image (for example, an average value of pixels in a region of interest) is fed back to the X-ray condition for fluoroscopy of a next frame, to make the statistical value to be close to a targeted value. For example, the X-ray condition, such as the X-ray tube voltage, the X-ray tube current, the pulse width, and the radiation quality filter, may be configured by the ABC as appropriate. Because the X-ray condition converged by the ABC reflects an average X-ray absorbance of the subject, by using a result of adjustment of the X-ray condition by the ABC, an entrance dose necessary for acquiring an image quality needed for a high-dose X-ray image can be estimated.

The image-data generating function 214 generates X-ray image data by using a detection signal detected by the X-ray detector 15, and stores it in the storage circuitry 24. Moreover, because the accuracy in identifying an amount of movement and a cycle of movement improves in a period constituted of plural heartbeats, which is, for example, about three heartbeats, the fluoroscopy may be performed in a period of three heartbeats, or more.

Estimation of Timing in which Periodic Movement is Small

At step S104, the identifying function 211 calculates an amount of movement and a cycle of movement in a fluoroscopic image through the image processing function 215 for respective positions in the fluoroscopic images constituted of plural frames that are acquired at step S103. The identifying function 211 reads the amount of movement and the cycle of movement based on the amount of movement at the respective positions in the X-ray images calculated by the image processing function 215 based on the generated X-ray images from the storage circuitry 24. At step S105, the identifying function 211 estimates in what timing the timing in which periodic movement is small (period in which movement is relatively small) starts and ends next, that is, start timing and end timing thereof.

Figure 4:
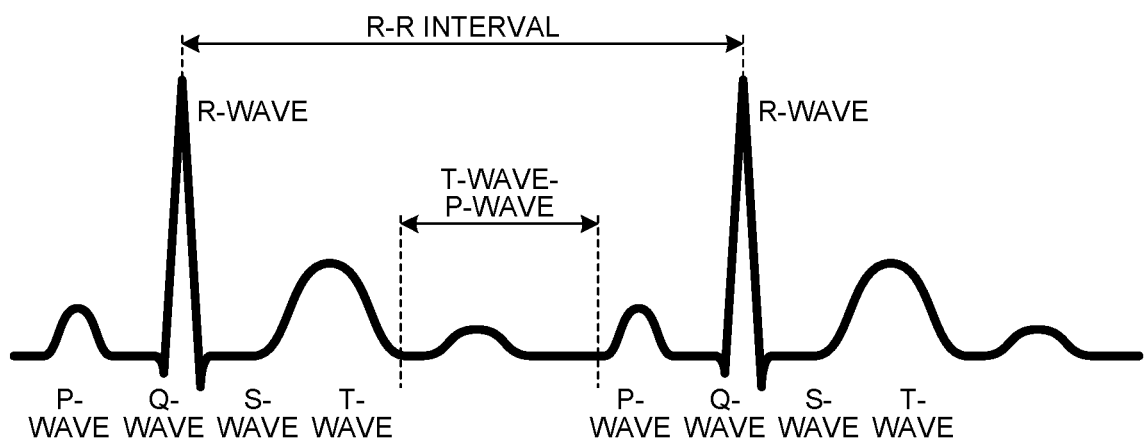
FIG. 4 is a diagram illustrating an example of an electrocardiogram and names of respective portions according to the first embodiment.

In the first embodiment, the identifying function 211 identifies the period in which movement is relatively small based on an amount of movement in a fluoroscopic image, without using electrocardiogram data. The period in which movement is relatively small corresponds, for example, a period in which fluctuation of an electrocardiogram in one heartbeat is relatively small, as a period between T wave and P wave in an electrocardiogram in FIG. 4. However, because the state of heartbeat of a subject changes every moment, the period in which fluctuation caused by heartbeats is small is not necessarily the period corresponding to the period between T wave and P wave. FIG. 4 is a diagram illustrating an example of an electrocardiogram and names of respective portions according to the first embodiment.

In the first embodiment, the X-ray diagnostic apparatus 1 identifies the period in which movement is relatively small based on an amount of movement in a fluoroscopic image rendering a state of heartbeat of the heart by irradiating an X-ray. The heart repeats contraction and expansion, and a period in which it is relatively at rest between contraction and expansion is the period in which fluctuation of electrocardiogram of one heartbeat is relatively small, and the period appears periodically in each heartbeat in a healthy human body. In the present embodiment, because the period in which movement is relatively small is identified from a fluoroscopic image constituted of plural frames, even when the frame rate at imaging is increased, it is difficult to observe the fluctuation by heartbeats completely, and it is not to strictly identify the period in which movement is relatively small.

The method of calculating an amount of movement by the image processing function 215 includes a method of calculating an amount of movement by performing inter-frame difference or optical flow with respective fluoroscopic images, which are plural frames of X-ray images sequentially collected. For example, when an amount of movement is calculated by the inter-frame difference, the image processing function 215 calculates an amount of movement between adjacent two frames in fluoroscopic images by performing the inter-frame difference between temporally adjacent frames of fluoroscopic images (plural frames) that are constituted of plural X-ray images sequentially collected. That is, the image processing function 215 calculates respective amounts of movement between the adjacent two frames described above for plural frames sequentially collected.

The image processing function 215 identifies transition in the amount of movement in plural frames based on the respective amounts of movement calculated between adjacent two frames, and calculates a cycle of movement based on the transition in the amount of movement. Specifically, the image processing function 215 calculates a cycle in which timing of small movement amount appears in the transition in the amount of movement. For example, the image processing function 215 extracts timing in which an amount of movement becomes less than a threshold, a period in which an amount of movement is continuously less than the threshold, and timing in which an amount of movement exceeds the threshold in transition in the amount of movement. Thus, the image processing function 215 calculates a cycle of the period in which an amount of movement is continuously smaller than the threshold in transition in the amount of movement.

The transition of the amount of movement described above may be calculated in an entire image, or may be calculated per region. Moreover, the threshold to be compared with the amount of movement can be determined arbitrarily. For example, the threshold to be compared with the amount of movement may be determined for each subject.

Furthermore, for example, when the amount of movement is calculated by the optical flow, the image processing function 215 identifies transition in the amount of movement based on a displacement vector that indicates movement of an object between temporally adjacent frames in plural frames. The image processing function 215 calculates a cycle of a period in which the amount of movement is continuously less than the threshold by extracting timing in which an amount of movement becomes less than a threshold, timing in which an amount of movement is continuously less than the threshold, and timing in which an amount of movement exceeds the threshold.

The identifying function 211 identifies appearance timing of the period in which movement is relatively small in a time axis of image collection based on the amount of movement and the cycle of movement calculated by the image processing function 215. For example, the identifying function 211 identifies a frame corresponding to a period in which the mount of movement calculated by the image processing function 215 is continuously less than the threshold. The identifying function 211 determines a frame corresponding to the timing in which the amount of movement becomes less than the threshold as start timing of the period in which movement is relatively small, and a frame corresponding to the timing in which the amount of movement exceeds the threshold as end timing of the period in which movement is relatively small.

Fluctuation caused by heartbeat is not constant all the time, and it can be considered to be different per heartbeat. Therefore, the identifying function 211 respectively extracts a frame corresponding to the start timing and a frame corresponding to the end timing of the period in which movement is relatively small described above, for plural frames corresponding to three heartbeats, and identifies appearance timing in the frames. That is, the identifying function 211 respectively extracts three frames corresponding to the start timing and three frames corresponding to the end timing of the period in which movement is relatively small, from among plural frames corresponding to three heartbeats.

The identifying function 211 estimates the start timing of the period in which movement is relatively small appearing thereafter, based on the appearance timing of the three frames extracted for the start timing. Moreover, the identifying function 211 estimates the end timing of the period in which movement is relatively small appearing thereafter, based on the appearance timing of the three frames extracted for the end timing. That is, when fluoroscopic images are consecutively collected, the identifying function 211 identifies a frame corresponding to the start timing of the period in which movement is relatively small appearing thereafter, and a frame corresponding to the end timing of the period in which movement is relatively small.

The identifying function 211 may perform preprocessing to appropriately calculate the amount of movement due to fluctuation caused by heartbeat in X-ray images through the image processing function 215. As an example of the preprocessing, for example, X-ray image data from which a background component, such as an organ and a bone, and a noise component is removed is generated, and an amount of movement is calculated based on the generated X-ray image data, thereby improving the accuracy of the amount of movement. Specifically, the image processing function 215 removes a low frequency component by subjecting the X-ray image data to filtering processing to remove a background component, to acquire the X-ray image data in which a signal component remains. Furthermore, the image processing function 215 removes a high frequency component that include lots of small noises likely to affect appropriate calculation of movement from the acquired X-ray image data, to acquire X-ray image data of an intermediate frequency component. By using X-ray image data thus acquired, it is possible to calculate an amount of movement, focusing on signal information including a subject to be observed in signal information included in an X-ray image.

Because an irradiation area is set in advance by an operator for a fluoroscopic image, which is an object for which an amount of movement is calculated, there is a low possibility that a region of interest is present at an edge portion of an X-ray image. Therefore, weights may be assigned according to coordinates in an image for the amount of movement such that a weighting coefficient decreases as it approaches an edge portion of the image. For example, when movement in an edge portion of an image is large, an amount of movement in the edge portion of the image can be larger than an amount of movement of a region of interest. Even in such a case, by performing weighting for the amount of movement, it is possible to prevent degradation of calculation accuracy of the amount of movement caused by movement in an edge portion of an image. Moreover, to calculate the amount of movement accurately, a frame rate in fluoroscopy may be increased.

Furthermore, when the object to be observed is a radiopaque device, the device can be rendered in an X-ray image without using a marker pair. Therefore, the image processing function 215 may calculate the amount of movement, limiting an area to the area including the device in the X-ray image. That is, the identifying function 211 may control the image processing function 215 to perform segmentation such that the radiopaque device and others are segmented in the X-ray image, to calculate the amount of movement, limiting to the area. Thus, by calculating the amount of movement, limiting an object to a periphery of the radiopaque device, which is the object to be observed, and by identifying a period in which movement is relatively small from a cycle of movement, the identifying function 211 can avoid influence from movement of portions other than the object to be observed. Furthermore, the identifying function 211 can reduce time necessary for calculation of the amount of movement.

Determination of Pulse Width

Figure 5:
FIG. 5 is a diagram illustrating an example relating to determination of a pulse width according to the first embodiment.

At step S106, the determining function 212 determines a pulse width of an X-ray to be irradiated at step S110 according to the identified period in which periodic movement is small and the X-ray condition input in advance by the input interface 22. The pulse width is a period in which an X-ray is pulse-irradiated to acquire one piece of X-ray image. FIG. 5 is a diagram illustrating an example relating to determination of a pulse width according to the first embodiment. For example, when the irradiation control function 213 performs fluoroscopy for three heartbeats, the identifying function 211 identifies a period in which movement is periodically small while one heartbeat thereafter is made. As illustrated in FIG. 5, the determining function 212 sets the pulse width of an X-ray to be included in the period in which movement is periodically small.

For example, the determining function 212 determines a pulse width such that X-ray irradiation is performed in a period in which movement is relatively small and observation of the device is easy in a fluoroscopic image, according to periodic movement of the subject in a period from four heartbeats before until two heartbeats before as illustrated in FIG. 5. However, because there is a limit for a realistic pulse value due to device specifications, such as output power of the X-ray tube 12 and the like, the determining function 212 may be unable to set the pulse width to be smaller than the period in which periodic movement is small.

A minimum value and a maximum value of the pulse width may be set in advance by an operator through the input interface 22. For example, when a dose of an X-ray output by the X-ray tube 12 is determined, setting a pulse width guaranteeing an output of the dose as the minimum value, a pulse width may be limited not to be smaller than the minimum value.

Moreover, the pulse width may be determined based on an adjustment result by the ABC when the X-ray condition for fluoroscopy is determined by the ABC at step S103. For example, the determining function 212 may calculate an entrance dose necessary for acquiring an image quality needed for a high-dose X-ray image, and may set the pulse width such that a pulse of the X-ray is included in the identified period in which periodic movement is small, and that the necessary entrance dose can be obtained according to the device specifications (that is, restrictions relating to applicable X-ray conditions).

Alternatively, the determining function 212 may determine the pulse width from a relationship between a pulse width in fluoroscopy and motion blur in one frame of a fluoroscopic image. That is, the determining function 212 determines the pulse width in X-ray irradiation of a relatively high dose performed by the imaging device 10 at step S110 based on a pulse width at fluoroscopy and motion blur that occurs in one frame of fluoroscopic image, in a fluoroscopic image constituted of plural X-ray images sequentially collected. A calculation method of motion blur may be a known method.

The pulse width is a value input in advance through the input interface 22, or a value set by the ABC, and the determining function 212 acquires a pulse width for fluoroscopy from the storage circuitry 24. Moreover, the determining function 212 acquires motion blur occurring in each frame of the fluoroscopic image calculated by the image processing function 215, for fluoroscopic images that have been acquired in the period in which movement is relatively small identified by the identifying function 211 using fluoroscopic images.

The determining function 212 compares the motion blur of the fluoroscopic image calculated by the image processing function 215 with an allowable value of motion blur. The allowable value of motion blur is a value of motion blur that is allowable in a high-dose X-ray image, and is set in advance by the operator. The determining function 212 can determine a pulse width of X-ray irradiation of a relatively high dose performed at step S110 based on a relationship between a motion blur of a fluoroscopic image when a pulse width in fluoroscopy is one numerical value. A fluoroscopic image that is compared with the allowable value of motion blur is not limited to a fluoroscopic image corresponding to the period in which movement is relatively small, but may be a fluoroscopic image of entire period in which the fluoroscopy is performed.

For example, when the motion blur of the fluoroscopic image is lower than the allowable value, the determining function 212 determines a pulse width of X-ray irradiation of a relatively high dose to the same value as the pulse width of fluoroscopy. Moreover, when the motion blur of the fluoroscopic image exceeds the allowable value, the determining function 212 determines a pulse width of X-ray irradiation of a relatively high dose to a value smaller than the pulse width of fluoroscopy. That is, when the motion blur of the fluoroscopic image is lower than the allowable value, the determining function 212 determines the pulse width, determining that the pulse width of X-ray irradiation of a relatively high dose may be set to the same value as the pulse width in fluoroscopy. Moreover, when the motion blur of the fluoroscopic image exceeds the allowable value, the determining function 212 determines the pulse width, determining that the pulse width used when fluoroscopy has been performed is insufficient because it would cause the same motion blur also in X-ray irradiation of a relatively high dose, and changes the pulse width to a small value for the X-ray irradiation of a relatively high dose.

For example, when fluoroscopy in which a pulse width is set to A is performed in a period of three heartbeats, at step S103, fluoroscopic images constituted of plural frames corresponding to three heartbeats are sequentially collected. The determining function 212 then acquires a fluoroscopic image that corresponds to a period in which movement is relatively small out of the fluoroscopic images constituted of the plural frames of three heartbeats. For example, out of the fluoroscopic images, when five frames of fluoroscopic images are present in a period in which movement is relatively small of the first heartbeat, the determining function 212 determines whether each motion blur is lower than the allowable value for the five frames of fluoroscopic images. If the motion blur of all five frames are lower than the allowable value, it can be determined that fluoroscopy performed in the period in which movement is relatively small of the first heartbeat is performed without causing motion blur that exceeds the allowable value. The determining function 212 performs this determination similarly for the three heartbeats, and determines whether fluoroscopy performed in three periods in which movement is relatively small has been performed without causing motion blur that exceeds the allowable value.

When it is found that each motion blur in the fluoroscopic images corresponding to the periods in which movement is relatively small of three heartbeats exceeds the allowable value as a result of determining whether it is lower than the allowable value, its cause can be considered that the pulse width A in fluoroscopy is large. Accordingly, the determining function 212 sets a pulse width in X-ray irradiation of a relatively high dose to be smaller, for example, to about 80% of the pulse width A in the fluoroscopy. However, because the state of heartbeat of the subject changes every moment, the period in which movement is relatively small at the time when the fluoroscopy is performed gradually changes, and the period can be earlier or later at the time when X-ray irradiation of a relatively high dose is to be performed. Therefore, timing in which X-ray irradiation of a relatively high dose is performed (irradiation start timing) may be changed based on a value of motion blur that exceeds the allowable value and the frequency of excess.

Determination of Other X-Ray Conditions

At step S107, the determining function 212 determines X-ray conditions other than the pulse width (other X-ray conditions). Specifically, the determining function 212 determines an X-ray tube voltage, an X-ray tube current, a focal spot size, a radiation quality filter, and a targeted dose intended to be detected by a detector. The determining function 212 determines the focal spot size and the X-ray tube voltage in priority in the X-ray conditions, to acquire a dose necessary for X-ray irradiation according to the pulse width determined at step S105. A determination method of the X-ray condition may be same as the determination method of ordinary X-ray conditions. Moreover, the determining function 212 may determine the X-ray condition according to a preset input through the input interface 22 by the operator. Alternatively, when the X-ray condition of fluoroscopy is determined by the ABC at step S103, the determining function 212 may determine the other X-ray conditions based on the adjustment result by the ABC. For example, when an entrance dose necessary for high-dose X-ray irradiation is calculated based on the adjustment result by the ABC, and a pulse width is set according thereto at step S103, the determining function 212 may determine the other X-ray conditions such that the entrance dose necessary with the set pulse width is obtained.

The determining function 212 determines the focal spot size and the X-ray tube voltage in priority among the other X-ray conditions, following the pulse width determined at step S106. For the focal spot size and the X-ray tube voltage, the determining function 212 may set the focal spot size small to prevent the focal spot being out of focus, and may set the X-ray tube voltage not to be too high, similarly to the case of normal X-ray condition determination. Moreover, the X-ray diagnostic apparatus has several kinds (for example, three kinds) of focal spot sizes. Accordingly, the determining function 212 determines the focal spot size, for example, by selecting from among the three kinds according to the pulse width determined at step S106 to obtain the targeted dose of an X-ray.

Arrangement of Pulse

As described above, the determining function 212 determines the pulse width such that the pulse width is smaller than periodic movement. Fluctuation by heartbeats, of course, includes a period in which movement is relatively large. That is, before and after a period in which movement is relatively small, there is a period in which movement is relatively large, and the period in which movement is relatively large and the period in which movement is relatively small occur alternately. Therefore, there is a higher possibility of receiving an influence of movement as it is closer to start timing and end timing of the period in which movement is relatively small.

Therefore, the irradiation control function 213 arranges a pulse so as not to be affected by movement before and after the period in which movement is relatively small. That is, the irradiation control function 213 determines the irradiation start timing such that movement before and after the period in which movement is relatively small does not affect the pulse, the pulse width of which has been determined by the determining function 212. For example, the irradiation control function 213 determines that start timing of the period in which movement is relatively small to [when 0% of the period in which movement is relatively small has elapsed], and end timing of the period in which movement is relatively small to [when 100% of the period in which movement is relatively small has elapsed]. In such a case, the irradiation control function 213 determines the irradiation start timing by arranging a pulse to be positioned such that the center of pulse is positioned at an elapsed time percentage (for example, 50%) set in the period in which movement is relatively small.

Furthermore, also in the period in which movement is relatively small, small movement timing and large movement timing are included. The irradiation control function 213 can control to perform X-ray irradiation, avoiding a period with large fluctuation in the period in which movement is relatively small, to generate an X-ray image of a higher visibility.

To perform X-ray irradiation, avoiding the period with large fluctuation in the period in which movement is relatively small, for example, the irradiation control function 213 determines irradiation start timing of an X-ray based on an amount of movement between start timing and end timing of the period in which movement is relatively small when determining the irradiation start timing. For example, the irradiation control function 213 determines that the start timing of the period in which movement is relatively small to [when 0% of the period in which movement is relatively small has elapsed], and the end timing of the period in which movement is relatively small to [when 100% of the period in which movement is relatively small has elapsed]. It is herein assumed that fluctuation is large in a period in which 0% to 10% of the period in which movement is relatively small has elapsed. Moreover, the determined pulse width is assumed to be length of 80% of the period in which movement is relatively small.

In this case, the irradiation control function 213 determines the irradiation start timing to, for example, a point when [20% of the period in which movement is relatively small has elapsed], to avoid the period in which 0% to 10% of the period in which movement is relatively small has elapsed. When the irradiation start timing is determined as described above, the start timing of X-ray irradiation is to be a point of time when 20% of the period in which movement is relatively small has elapsed, and the end timing is to be a point of time when 100% of the period in which movement is relatively small has elapsed.

When the pulse width determined by the determining function 212 exceeds length of the period in which movement is relatively small, the irradiation control function 213 arranges a pulse so as to be able to avoid an influence of movement. In such a case, for example, the irradiation control function 213 refers to an amount of movement in frames before and after the period in which movement is relatively small, and determines the irradiation start timing such that a pulse is arranged on a small movement side.

Determination of Irradiation-Control Start Timing and Irradiation Start Timing

At step S108, the irradiation control function 213 determines the irradiation-control start timing and the irradiation start timing based on delay time that is necessary until an X-ray is actually irradiated from when the irradiation control signal of an X-ray is output. The irradiation-control start timing and the irradiation start timing determined by the irradiation control function 213 will be applied to X-ray irradiation control performed at step S110.

Figure 6:
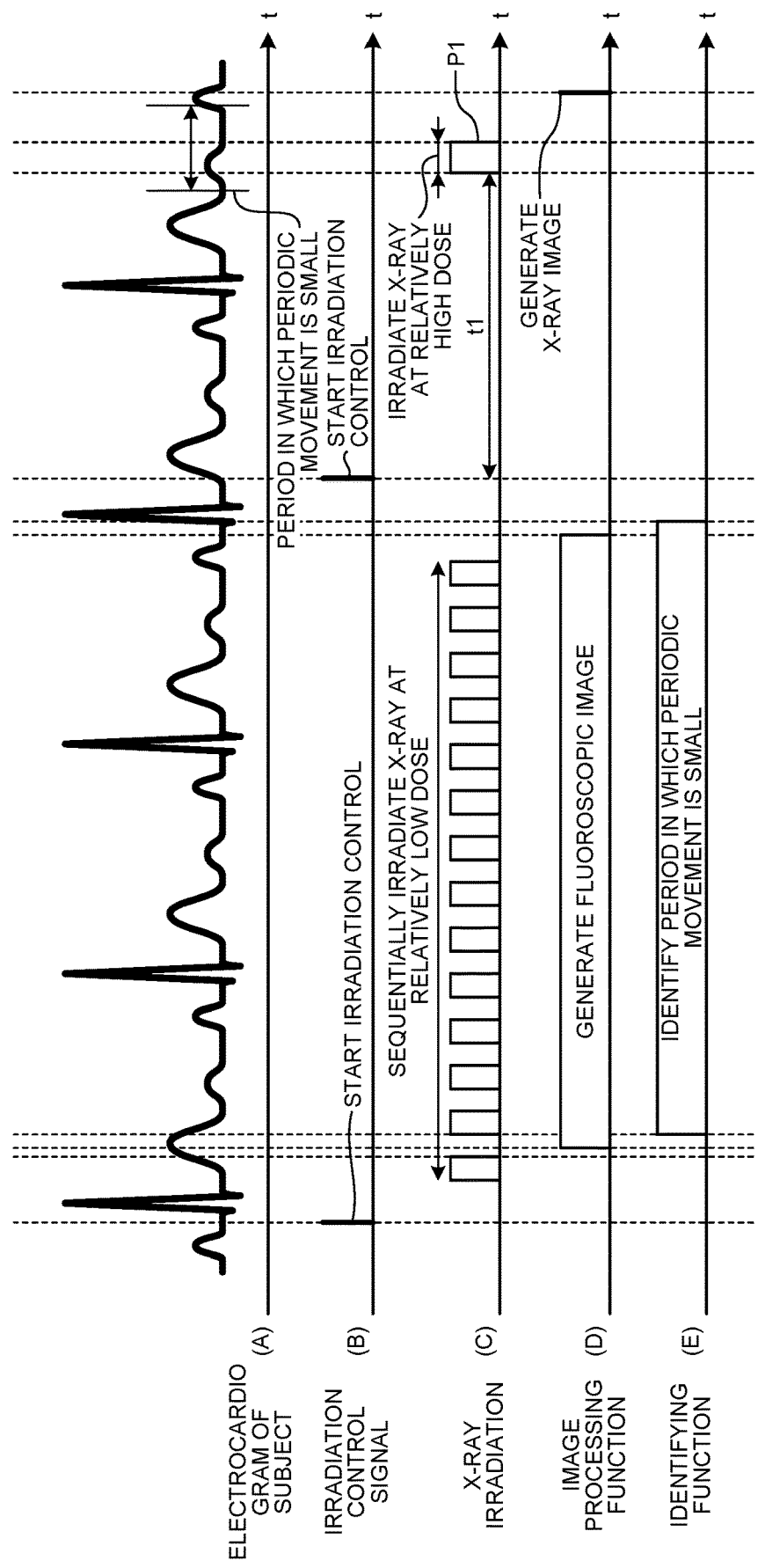
FIG. 6 is a diagram illustrating an example of a time chart according to the first embodiment, to calculate irradiation-control start timing backward, considering delay time.

FIG. 6 is a diagram illustrating an example of a time chart according to the first embodiment, to calculate the irradiation-control start timing backward, considering the delay time. In FIG. 6, an electrocardiogram (A) of the subject is shown to show movement by heartbeats of the heart of the subject in an X-ray image, but an electrocardiogram is not used in the present embodiment.

An irradiation control signal (B) in FIG. 6 indicates a signal that is output by the irradiation control function 213, and an X-ray is irradiated according to the irradiation control signal (B). Moreover, X-ray irradiation (C) in FIG. 6 indicates irradiation of an X-ray that is emitted from the X-ray tube 12 according to the irradiation control signal (B). Furthermore, an image processing function (D) in FIG. 6 corresponds to the processing performed by the image processing function 215, and indicates generation of an X-ray image (fluoroscopic image, X-ray image collected at a relatively high dose, and the like) according to the X-ray irradiation (C). Furthermore, an identifying function (E) in FIG. 6 corresponds to the processing performed by the identifying function 211, and indicates identification of a period in which movement is relatively small based on a fluoroscopic image generated by the image processing function (D).

For example, the X-ray diagnostic apparatus 1 according to the first embodiment outputs the irradiation control signal (B) to start irradiation control, and thereby irradiates X-rays sequentially at a relatively low dose in the set pulse width as indicated by the X-ray irradiation (C) in FIG. 6. In FIG. 6, only one irradiation control signal (B) to collect a fluoroscopic image is shown, but irradiation control signals to irradiate respective pulses are output in an actual situation.

The X-ray diagnostic apparatus 1 then generates fluoroscopic images corresponding to respective pulses according to the X-ray irradiation sequentially performed, and identifies a period in which movement is relatively small based on the generated fluoroscopic images. In the first embodiment, the period in which periodic movement is small is identified based on a fluoroscopic image. Therefore, the irradiation control function 213 determines the irradiation start timing described above based on information indicating of which X-ray irradiation on a time axis the fluoroscopic images identified as the period in which periodic movement is small are, and thus can cause X-ray irradiation in the period in which periodic movement is small in the actual body of the subject. Accordingly, for example, as indicated by the X-ray irradiation (C) in FIG. 6), a pulse P1 is to be set to the period in which a periodic movement is small in the actual body of the subject.

Furthermore, the irradiation control function 213 determines the irradiation-control start timing such that pulse irradiation is performed in the period in which periodic movement is small in the actual body of the subject. In the X-ray diagnostic apparatus 1, there is delay time (time t1 in FIG. 6) that is necessary until an X-ray is actually irradiated from when the irradiation control signal (B) is output. Therefore, to realize a pulse set for the period in which periodic movement is small in the actual body of the subject by the processing described above, it is necessary to consider the delay time that is necessary until an X-ray is actually irradiated from when the irradiation control signal of an X-ray is output.

Accordingly, the irradiation control function 213 determines a point of time previous to the start timing of pulse (irradiation start timing) set for the period in which periodic movement is small in the actual body of the subject by time t1, as the irradiation-control start timing. That is, the irradiation control function 213 outputs the irradiation control signal at the point of time previous to the start timing of pulse set for the period in which periodic movement is small in the actual body of the subject by time t1 as indicated by the irradiation control signal (B) in FIG. 6. Thus, an X-ray can be irradiated at a relatively high dose in the period in which periodic movement is small in the actual body of the subject.

The delay time (time t1) that is necessary until an X-ray is actually irradiated from when the irradiation control signal of an X-ray is output may be calculated from an actual control state in the X-ray diagnostic apparatus 1, or may be input in advance through the input interface 22.

Hi-Dose X-Ray Irradiation

At step S110, the irradiation control function 213 starts irradiation control at the irradiation-control start timing determined at step S108, and irradiates an X-ray in the irradiation start timing. Specifically, the irradiation control function 213 outputs a control signal to perform X-ray irradiation of a relatively high dose according to the X-ray condition, the irradiation-control start timing, and the irradiation start timing determined at step S106 to step S108. When the irradiation control function 213 outputs the control signal, the imaging device 10 performs X-ray irradiation of a relatively high dose.

Display of High-Dose X-Ray Image

At step S111, the display control function 217 displays an X-ray image of a relatively high dose (high-dose X-ray image) generated based on the detection signal detected by the X-ray detector 15 on the display 23. The operator observes the high-dose X-ray image displayed on the display.

When plural fluoroscopic images collected to determine the period in which movement is relatively small are temporarily stored, and to be displayed together with a high-dose X-ray image as a moving image, the interpolation-image generating function 216 may generate interpolation images. In such a case, for example, the interpolation-image generating function 216 identifies a fluoroscopic image that corresponds to a time phase between a fluoroscopic image that is collected last and the high-dose X-ray image out of the fluoroscopic images successively collected, and can generate an interpolation image by using the identified fluoroscopic image. The display control function 217 can display the interpolation image generated by the interpolation-image generating function 216.

Change of Condition of High-Dose X-Ray Irradiation

At step S112, the irradiation control function 213 determines whether a change input operation has been accepted in the input interface 22. For example, X-ray irradiation can be performed in timing affected by fluctuation caused by heartbeats due to some causes when a series of processing at step S101 to step S111 is performed, and a high-dose X-ray image is displayed on the display. In this case, first, the operator observes the high-dose X-ray image displayed on the display. When the operator determines that it is necessary to perform X-ray irradiation again, the operator makes an input to change the irradiation start timing or the X-ray conditions through the input interface 22. The input to change conditions is stored in the storage circuitry 24. The irradiation control function 213 acquires the input to change made by the operator from the storage circuitry 24, and controls to perform a series of processing from step S101 again according to the contents of the input to change.

For example, suppose that the operator determines that adjustment of the pulse width is necessary because motion blur has occurred in the high-dose X-ray image displayed on the display. In this case, the operator makes an input to change the pulse width with respect to the input interface 22. The X-ray diagnostic apparatus 1 performs the processing again.

In the embodiment described above, a case in which the period in which movement is relatively small is identified for fluoroscopic images corresponding to three heartbeats, the fourth heartbeat corresponds to processing time, and X-ray irradiation of a relatively high dose is performed at the fifth heartbeat has been explained. However, embodiments are not limited thereto. For example, processing may be performed according to the identification accuracy of the period in which movement is relatively small, or delay time that is necessary until an X-ray image is generated from when the X-ray irradiation control is started predetermined by specifications of the device, or the like. For example, the period in which movement is relatively small may be identified by using fluoroscopic image corresponding to a period of two heartbeats or less, or of four heartbeats or more. Furthermore, for example, after the period in which movement is relatively small is identified, processing time of two heartbeats or more may be given.

In the first embodiment described above, the processing circuitry 21, the driving circuitry 17, and the system control circuitry 18 may be handled as one unit, and this may be regarded as the "processing circuitry".

As described above, according to the first embodiment, the input interface 22 accepts an input operation performed by an operator. The identifying function 211 identifies a period in which periodic movement in an X-ray irradiation area is small. The irradiation control function 213 determines irradiation start timing of an X-ray according to the period in which periodic movement is small and controls to perform X-ray irradiation of a relatively high dose in the determined irradiation start timing, on condition that the input operation by the operator is being continued. Therefore, when the input operation by the operator is being continued, because the X-ray diagnostic apparatus 1 according to the first embodiment performs processing from identification of a period in which movement is relatively small based on periodic movement in an irradiation area and X-ray irradiation of a relatively high dose sequentially, it facilitates observation of a device by the operator without performing complicated operations.

Moreover, the X-ray diagnostic apparatus 1 according to the first embodiment observes the device in real time through a fluoroscopic image for the X-ray irradiation area in which fluctuation caused by heartbeats of the subject occurs, and identifies in which period in a next phase the period in which movement is relatively small occurs, and thereby determines the X-ray condition optimal according to the identified period, to perform high-dose X-ray irradiation. Therefore, the X-ray diagnostic apparatus 1 can acquire a high-dose X-ray image in optimal timing per subject according to a state of the subject, and enables to acquire an X-ray image with which observation of a device from any subject is facilitated.

Moreover, according to the first embodiment, the image-data generating function 214 sequentially generates X-ray images based on an X-ray that has emitted from the X-ray tube and has passed through the body of the subject. The identifying function 211 identifies a period in which periodic movement is small based on the X-ray images sequentially generated by the image-data generating function 214. Therefore, the X-ray diagnostic apparatus 1 according to the first embodiment irradiates an X-ray, and enables to identify in what phase the period in which periodic movement is small occurs next in real time, based on plural X-ray images sequentially generated.

Furthermore, according to the first embodiment, the determining function 212 determines the X-ray condition according to continuation of the input operation, based on the period in which periodic movement is small. Therefore, the X-ray diagnostic apparatus 1 according to the first embodiment can determine the X-ray condition, considering the period in which periodic movement is small, and enables to perform X-ray irradiation suitable for observation of a device.

Moreover, according to the first embodiment, the determining function 212 determines a pulse width according to length of the period in which periodic movement is small. Therefore, the X-ray diagnostic apparatus 1 according to the first embodiment can determine X-ray irradiation timing to a period that receives a small influence of movement, and enables to set the X-ray condition more suitable for observation of a device.

Furthermore, according to the first embodiment, the determining function 212 determines a focal spot size according to length of the period in which periodic movement is small and a targeted dose. Therefore, the X-ray diagnostic apparatus 1 can obtain a dose that receives a small influence of movement, to render a device appropriately, and enables to set the X-ray condition suitable for observation of a device.

Moreover, according to the first embodiment, the identifying function 211 calculates a degree of periodic movement in respective positions in an X-ray image based on plural X-ray images. Accordingly, the X-ray diagnostic apparatus 1 according to the first embodiment can calculate periodic movement at respective positions based on the X-ray images, and enables to accurately identify in which phase a period in which periodic movement is small occurs next.

Furthermore, according to the first embodiment, the identifying function 211 calculates a degree of movement based on a magnitude of periodic movement at respective positions in plural X-ray images, and on a weighting coefficient corresponding to respective positions. Therefore, the X-ray diagnostic apparatus 1 according to the first embodiment can determine the degree of movement in an appropriate area (area including a device, or the like) in an X-ray image, and enables to identify in which phase a period in which periodic movement is small occurs next accurately.

Moreover, according to the first embodiment, the determining function 212 determines a pulse width for X-ray irradiation at the time of generating plural X-ray images, and determines a pulse width for X-ray irradiation of a relatively high dose according to motion blur in the plural X-ray images. Therefore, the X-ray diagnostic apparatus 1 according to the first embodiment enables to determine a pulse width for X-ray irradiation of a relatively high dose based on a relationship between a pulse width in X-ray images actually collected and motion blur that is caused by X-ray irradiation, so as not to exceed an allowable value of motion blur, and enables to set the X-ray condition more suitable for X-ray irradiation of a relatively high dose.

Furthermore, according to the first embodiment, the irradiation control function 213 determines irradiation start timing according to time that is necessary until X-ray is actually irradiated from when an irradiation control signal of an X-ray of a relatively high dose is output. Therefore, the X-ray diagnostic apparatus 1 according to the first embodiment can determine a point of time when the irradiation control signal is output according to delay time that is necessary until an X-ray is actually irradiated from when the irradiation control signal of an X-ray is output, and enables to set the irradiation start timing to actually perform X-ray irradiation optimally.

Moreover, according to the first embodiment, the input interface 22 accepts an input operation to switch to the irradiation mode in which X-ray irradiation of a relatively high dose is performed, before accepting duration of an input operation. Therefore, the X-ray diagnostic apparatus 1 according to the first embodiment makes it easy for an operator to switch to a mode as necessary, and enables to change from the normal X-ray irradiation mode to the irradiation mode in which X-ray irradiation of a relatively high dose is performed without having performing a complicated operation.

Furthermore, according to the first embodiment, the input interface 22 accepts an input to change made by an operator relating to at least one of the irradiation start timing and the X-ray condition according to a state of an X-ray image of a relatively high dose acquired by X-ray irradiation of a relatively high dose. The irradiation control function 213 controls to perform X-ray irradiation of a relatively high dose in which at least one of the irradiation start timing and the X-ray condition is changed according to the input operation for change. Therefore, the X-ray diagnostic apparatus 1 according to the first embodiment can perform irradiation again according to the input for a change relating to X-ray irradiation, when the operator determines that X-ray irradiation of a relatively high dose is necessary to be performed again, and enables to perform re-irradiation suitable for observation of a device.

Moreover, according to the first embodiment, the display control function 217 causes the display 23 to display an X-ray image of a relatively high dose acquired by X-ray irradiation of a relatively high dose. Therefore, the X-ray diagnostic apparatus 1 according to the first embodiment can display the acquired X-ray image of a relatively high dose, and enables an operator to observe a device, and to determine whether re-irradiation is necessary.

Second Embodiment

In the first embodiment, a case of identifying a period in which fluctuation caused by heartbeats is small by using a fluoroscopic image has been explained as an example. In a second embodiment, a case of identifying a period in which fluctuation caused by heartbeats is small by using electrocardiogram data will be explained as an example. FIG. 6 is a block diagram illustrating an example of a configuration of the X-ray diagnostic apparatus 1 according to the second embodiment. The X-ray diagnostic apparatus 1 according to the second embodiment differs in a point in which an electrocardiograph 2 is connected to the X-ray diagnostic apparatus 1, and the X-ray diagnostic apparatus 1 acquires electrocardiogram data by the electrocardiograph 2 through acquiring circuitry 30, and processing performed by the identifying function 211 and the irradiation control function 213, from the X-ray diagnostic apparatus 1 according to the first embodiment. In the following, these points will be mainly explained.

Figure 7:
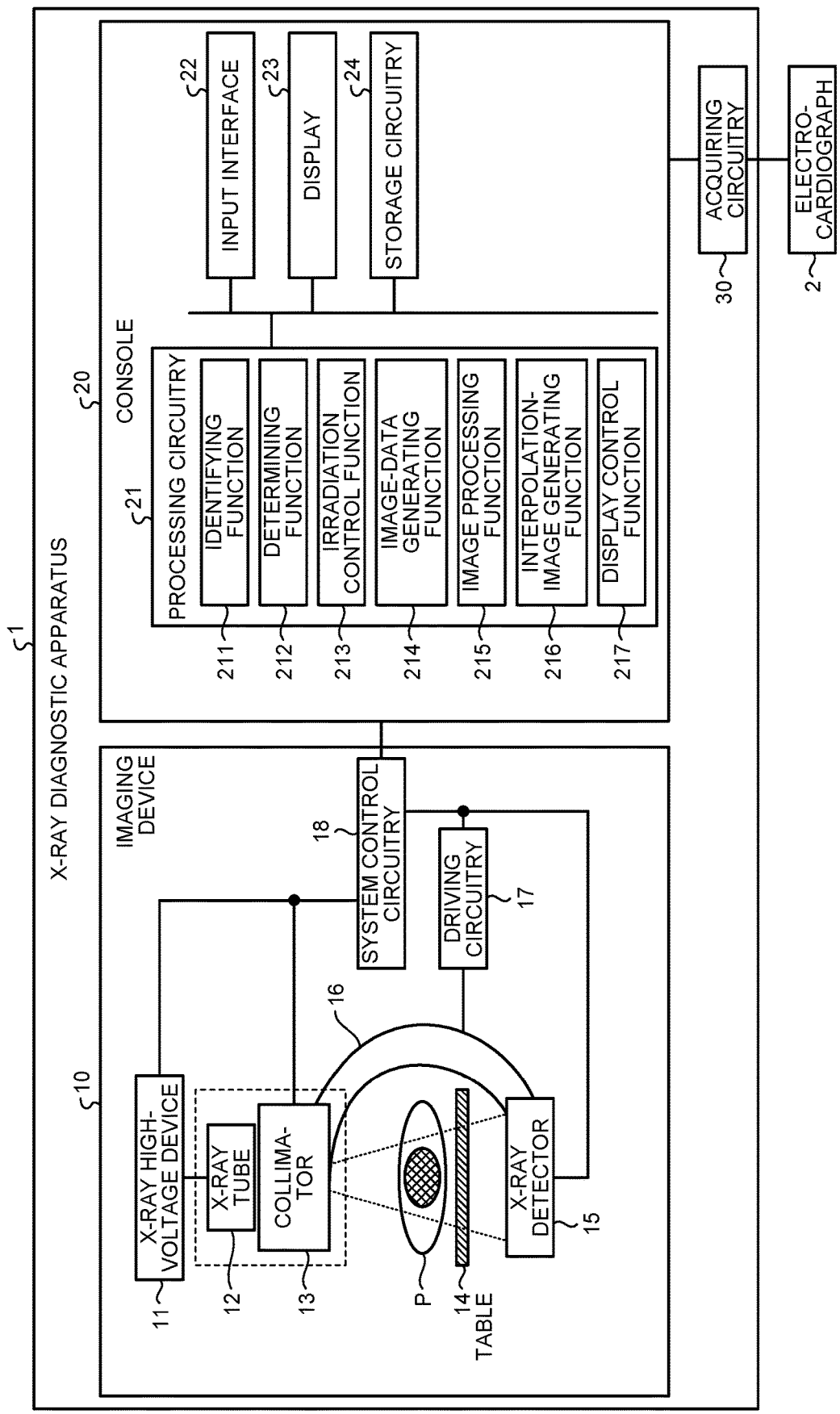
FIG. 7 is a block diagram illustrating an example of a configuration of an X-ray diagnostic apparatus according to a second embodiment.

As illustrated in FIG. 7, the X-ray diagnostic apparatus 1 according to the second embodiment has the electrocardiograph 2 connected thereto, and the X-ray diagnostic apparatus 1 acquires electrocardiogram data by the electrocardiograph 2 through the acquiring circuitry 30. The electrocardiogram data includes an electrocardiogram of a subject that is measured by the electrocardiograph 2, and timestamp data recording a time at which the electrocardiogram occurs.

The electrocardiograph 2 acquires electrocardiogram data of a subject, and transmits the acquired electrocardiogram data to the acquiring circuitry 30 together with timestamp data. The acquiring circuitry 30 is connected to the console 20, acquires the electrocardiogram data collected by the electrocardiograph 2, and stores the electrocardiogram data in the storage circuitry 24 of the console 20. The acquiring circuitry 30 can store information about a time at which the cardiogram data is acquired, associating with the electrocardiogram data.

The identifying function 211 according to the second embodiment determines a period in which periodic movement is small based on an electrocardiogram of a subject. The irradiation control function 213 according to the second embodiment determines irradiation-control start timing and irradiation start timing for the period in which periodic movement is small determined by using the electrocardiogram.

Figure 8:
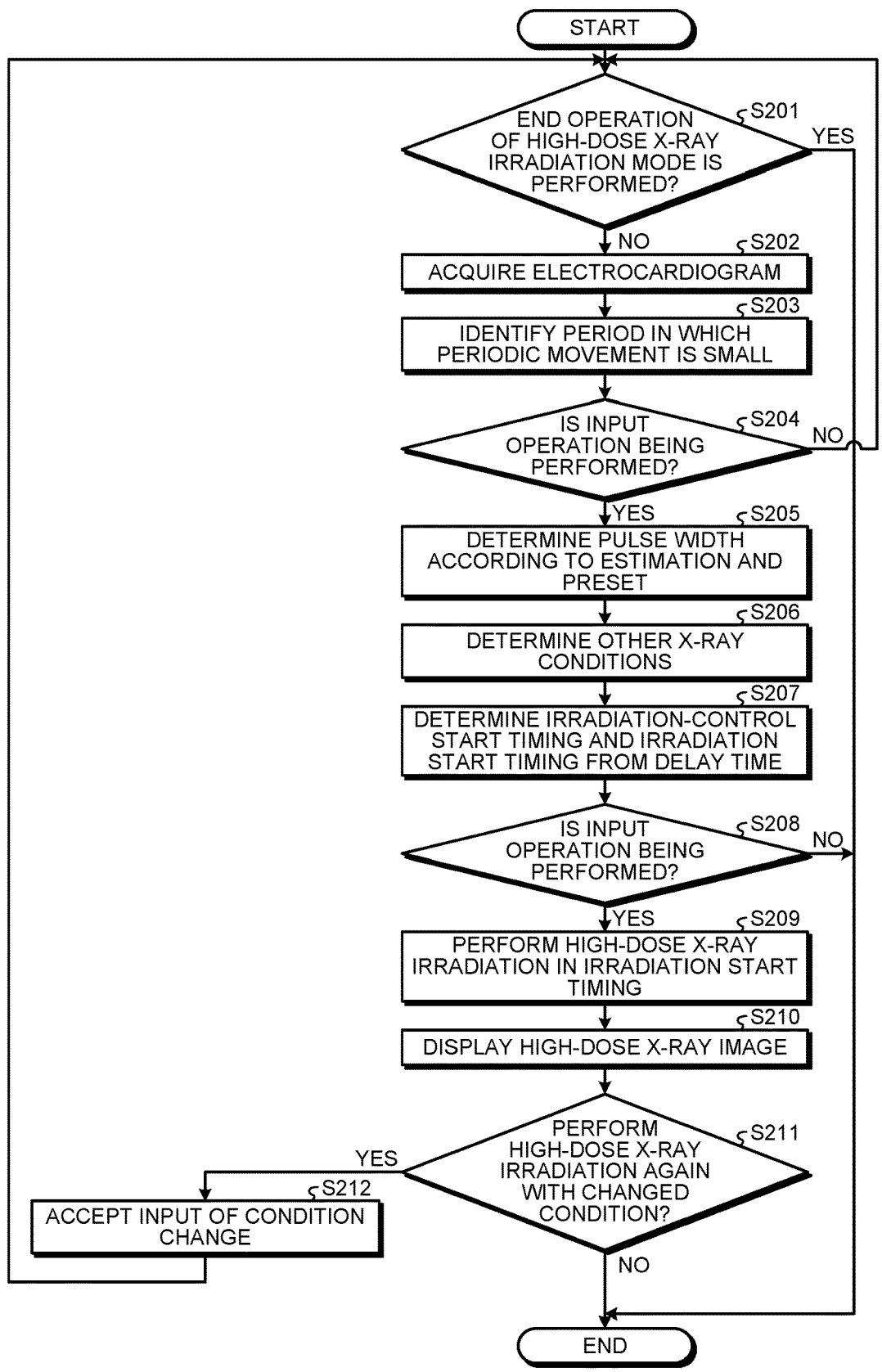
FIG. 8 is a flowchart illustrating a procedure of processing performed by the X-ray diagnostic apparatus according to the second embodiment.

First, a procedure of processing performed by the X-ray diagnostic apparatus according to the second embodiment will be explained. FIG. 8 is a flowchart illustrating the procedure of processing performed by the X-ray diagnostic apparatus 1 according to the second embodiment. In the procedure of processing illustrated in FIG. 8, an example in which the processing is ended when it is determined that an input operation is not being performed in determination whether an input operation is being performed by an operator will be explained, but it may be configured to return the processing flow to a start point when it is determined that the input operation is not being performed in the determination described above.

Step S201 in FIG. 8 is implemented by the processing circuitry 21 reading and executing a program corresponding to the irradiation control function 213 from the storage circuitry 24. Moreover, step S202 is implemented by the acquiring circuitry 30 reading and executing a corresponding program from the storage circuitry 24. Furthermore, step S203 is implemented by the processing circuitry 21 reading and executing a program corresponding to the identifying function 211 from the storage circuitry 24. Furthermore, step S204 is implemented by the processing circuitry 21 reading and executing a program corresponding to the irradiation control function 213 from the storage circuitry 24.

Moreover, step S205 to step S206 are implemented by the processing circuitry 21 reading and executing a program corresponding to the determining function 212 from the storage circuitry 24. Furthermore, step S207 to step S209 are implemented by the processing circuitry 21 reading and executing a program corresponding to the irradiation control function 213 from the storage circuitry 24. Moreover, step S210 is implemented by the processing circuitry 21 reading and executing a program corresponding to the display control function 217, the image-data generating function 214, and the image processing function 215 from the storage circuitry 24. Furthermore, step S211 to step S212 are implemented by the processing circuitry 21 reading and executing a program corresponding to the irradiation control function 213 from the storage circuitry 24.

As illustrated in FIG. 8, in the X-ray diagnostic apparatus 1 according to the second embodiment, the processing circuitry 21 determines whether an end operation of the high-dose X-ray irradiation mode has been made (step S201). When the end operation has been performed (step S201: YES), the X-ray diagnostic apparatus 1 ends the processing. On the other hand, when the end operation of the high-dose X-ray irradiation mode has not been performed (step S201: NO), the acquiring circuitry 30 acquires electrocardiogram data (step S202). The processing circuitry 21 identifies next timing in which a period in which movement is relatively small occurs based on the electrocardiogram data (step S203). When the input interface 22 accepts an input operation, the processing circuitry 21 determines that the input operation is being continued (step S204). When the input operation is not being continued (step S204: NO), the processing circuitry 21 returns to step S201, and continues to determine whether a continuous input operation is accepted.

On the other hand, when the input operation is being continued (step S204: YES), the processing circuitry 21 determines a pulse width of an X-ray to be irradiated at step S209 described later according to the period in which the identified periodic movement is small and the X-ray condition (preset) input in advance by the input interface 22 (step S205). Furthermore, the processing circuitry 21 determines X-ray conditions other than the pulse width (step S206).

Subsequently, the processing circuitry 21 determines irradiation-control start timing and irradiation start timing based on delay time that is necessary until an X-ray is actually irradiated from when the irradiation control signal of an X-ray is output, and on delay time that is necessary until an electrocardiogram is transferred to the acquiring circuitry 30 from when it is acquired by the electrocardiograph 2 (step S207). The processing circuitry 21 determines whether an input operation is being performed (step S208), and ends the processing when the input operation is not being performed (step S208: NO). On the other hand, when the input operation is being performed (step S208: YES), the processing circuitry 21 controls the imaging device 10 according to the irradiation start timing determined at step S207, to perform high-dose X-ray irradiation (step S209).

The processing circuitry 21 generates a high-dose X-ray image by using a detection signal that is detected by the imaging device 10 irradiating an X-ray of a relatively high dose, and displays the generated high-dose X-ray image on the display 23 (step S210).

Subsequently, the processing circuitry 21 determines whether the input interface 22 has accepted an input to perform high-dose X-ray irradiation again, changing a condition (step S211). When the input to perform high-dose X-ray irradiation with a changed condition has been accepted (step S211: YES), the processing circuitry 21 accepts the input to change a condition (step S212). The processing circuitry 21 then returns to step S201 and performs the processing.

On the other hand, when the input to perform high-dose X-ray irradiation with a changed condition is not accepted (step S211: NO), the processing circuitry 21 ends the processing relating to the high-dose X-ray irradiation mode.

Identification of Timing in which Periodic Movement is Small

As described above, at step S203, the identifying function 211 according to the second embodiment identifies a period in which movement is relatively small based on an electrocardiogram data of a subject. Specifically, the identifying function 211 identifies the period in which movement is relatively small based on electrocardiogram data that is obtained by the electrocardiograph 2 collecting electrocardiogram of the subject all the time, and that is acquired by the acquiring circuitry 30, and stores the identified result in the storage circuitry 24. In the second embodiment, the period in which movement is relatively small corresponds to a period in which fluctuation in electrocardiogram of one heartbeat is relatively small, as the period between T-wave and P-wave in the electrocardiogram in FIG. 4.

For example, the identifying function 211 identifies T-wave and P-wave in an electrocardiogram acquired by the acquiring circuitry 30. The identifying function 211 identifies timing in which T-wave fully falls as start timing of the period in which periodic movement is small, and identifies timing just before a rise of P-wave as end timing of the period in which periodic movement is small.

However, when an electrocardiogram cannot be collected at high accuracy by some influence, the identifying function 211 may identify the period in which periodic movement is small based on a period in which movement is relatively large and is an electrocardiogram is generally easy to be collected, as a period between R-wave and R-wave (R-R interval). For example, when the period in which periodic movement is small is to be identified based on "R-R interval" of an electrocardiogram, the identifying function 211 identifies R-wave in an electrocardiogram acquired by the acquiring circuitry 30. The identifying function 211 calculates a cycle in an electrocardiogram from length of "R-R interval", and identifies the period in which periodic movement is small by collecting relative movement size from fluctuation in the electrocardiogram.

The identifying function 211 may be configured to perform identification of the period in which periodic movement is small soon after the electrocardiograph 2 is set on the subject, and to perform the identification processing continuously. Alternatively, the identifying function 211 may be configured to identify the period in which periodic movement is small after a point of time when the input operation is made by the operator, not identifying the period in which periodic movement is small all the time.

Determination of Irradiation-Control Start Timing and Irradiation Start Timing

As described above, when the period in which periodic movement is small is identified by the identifying function 211, the determining function 212 determines a pulse width and other X-ray conditions, similarly to the first embodiment. The irradiation control function 213 arranges a pulse to the period in which movement is relatively small, similarly to the first embodiment.

At step S207, the irradiation control function 213 determines the irradiation-control start timing and the irradiation start timing based on the delay time that is necessary until an X-ray is actually irradiated from when the irradiation control signal of an X-ray is output, and on delay time that is necessary until an electrocardiogram is transferred to the acquiring circuitry 30 from when the electrocardiogram is acquired by the electrocardiograph 2.

Figure 9:
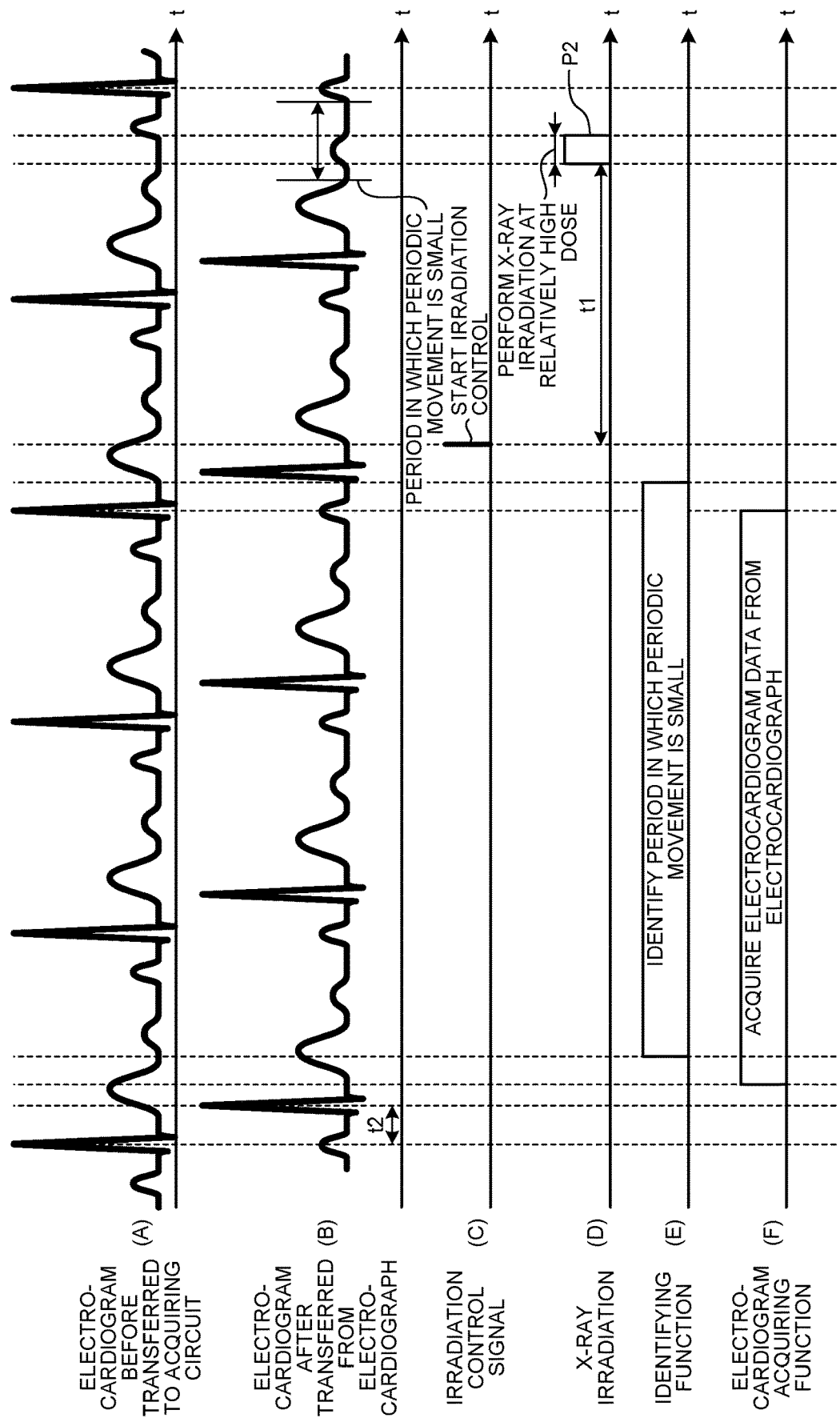
FIG. 9 is a diagram illustrating an example of a time chart according to the second embodiment, to calculate irradiation-control start timing backward, considering delay time.

FIG. 9 is a diagram illustrating an example of a time chart according to the second embodiment, to calculate irradiation-control start timing backward, considering delay time. An electrocardiogram (A) in FIG. 9 shows an electrocardiogram acquired by the electrocardiograph 2 before transferred to the acquiring circuitry 30. Moreover, an electrocardiogram (B) in FIG. 9 shows an electrocardiogram after transferred to the acquiring circuitry 30. As described above, in the second embodiment, the period in which movement is relatively small is identified based on an electrocardiogram, and a transferred electrocardiogram shows a waveform delayed by transfer time (time t2 in FIG. 9) from the electrocardiogram acquired from the subject as illustrated in FIG. 9.

An irradiation control signal (C) in FIG. 9 indicates a signal that is output by the irradiation control function 213, and an X-ray is irradiated according to the irradiation control signal (C). Moreover, X-ray irradiation D in FIG. 9 indicates irradiation of an X-ray that is emitted from the X-ray tube 12 according to the irradiation control signal (C). Furthermore, an identifying function (E) in FIG. 9 corresponds to the processing performed by the identifying function 211, and identifies a period in which periodic movement is small based on an electrocardiogram. Moreover, an electrocardiogram acquiring function (F) in FIG. 9 corresponds to the processing performed by the acquiring circuitry 30, and indicates acquisition of an electrocardiogram from the electrocardiograph 2.

For example, the X-ray diagnostic apparatus 1 according to the second embodiment acquires the electrocardiogram (B) in FIG. 9 by acquiring electrocardiogram data all the time by the acquiring circuitry 30. That is, the acquiring circuitry 30 acquires the electrocardiogram shown in (B) in FIG. 9 by consecutively acquiring signals in respective timings from the electrocardiograph 2.

The X-ray diagnostic apparatus 1 identifies the period in which periodic movement is small based on the acquired electrocardiogram (B). As described above, the acquired electrocardiogram (B) shows a waveform delayed by the transfer time from the actual electrocardiogram (A) of the subject. Accordingly, the irradiation control function 213 shifts the pulse set for the period in which periodic movement is small identified by the identifying function 211 to an earlier time by using the time t2 in FIG. 9, thereby adjusting it such that the pulse is set to the period in which periodic movement is small in the actual body of the subject. That is, the irradiation control function 213 sets pulse P2 to the period in which periodic movement is small in the actual body of the subject by shifting pulse P2 shown in the X-ray irradiation (C) in FIG. 9 backward by time t2.

Furthermore, the irradiation control function 213 determines the irradiation-control start timing such that pulse irradiation is performed in the period in which periodic movement is small in the actual body of the subject, similarly to the first embodiment. That is, the irradiation control function 213 determines a point of time earlier by time t1 from the start timing of pulse (X-ray irradiation start timing) set for the period in which periodic movement is small in the actual body of the subject, as the irradiation-control start timing.

The delay time that is necessary until an electrocardiogram is transferred to the acquiring circuitry 30 from when the electrocardiogram is acquired may be calculated from a difference between timestamp information given by the electrocardiograph 2 and time information given by the acquiring circuitry 30, or may be input through the input interface 22 in advance.

In the second embodiment described above, the processing circuitry 21, the driving circuitry 17, the system control circuitry 18, and the acquiring circuitry 30 may be regarded as one unit, and this can be understood as "processing circuitry".

As described above, according to the second embodiment, the identifying function 211 identifies a period in which periodic movement is small based on electrocardiogram data. Therefore, the X-ray diagnostic apparatus 1 according to the second embodiment enables identification of the period in which periodic movement is small by using information that is acquired normally in vascular interventional treatments.

Moreover, according to the second embodiment, the acquiring circuitry 30 acquires electrocardiogram data from the electrocardiograph 2. The irradiation control function 213 determines irradiation start timing according to time until the acquiring circuitry 30 acquires a signal from when the electrocardiograph 2 outputs the signal. Therefore, the X-ray diagnostic apparatus 1 according to the second embodiment can identify the period in which periodic movement is small, considering the transfer time of electrocardiogram data, and enables accurate identification of a period.

Third Embodiment

In a third embodiment, a case of identifying a period in which fluctuation by heartbeat is small by using a fluoroscopic image and electrocardiogram data will be explained as an example. The X-ray diagnostic apparatus 1 according to the third embodiment differs in processing performed by the identifying function 211 from the X-ray diagnostic apparatus 1 according to the second embodiment. In the following, this point will be mainly explained.

The identifying function 211 according to the third embodiment identifies the period in which periodic movement is relatively small based on plural X-ray images and electrocardiogram data. Specifically, the identifying function 211 identifies the period in which periodic movement is relatively small by using plural fluoroscopic images explained in the first embodiment and cardiogram data explained in the second embodiment. That is, the X-ray diagnostic apparatus according to the third embodiment has a configuration similar to the X-ray diagnostic apparatus 1 according to the second embodiment, and acquires plural fluoroscopic images and electrocardiogram data. The identifying function 211 identifies a period in which periodic movement is relatively small by using the acquired fluoroscopic images and electrocardiogram data.

Figure 10:
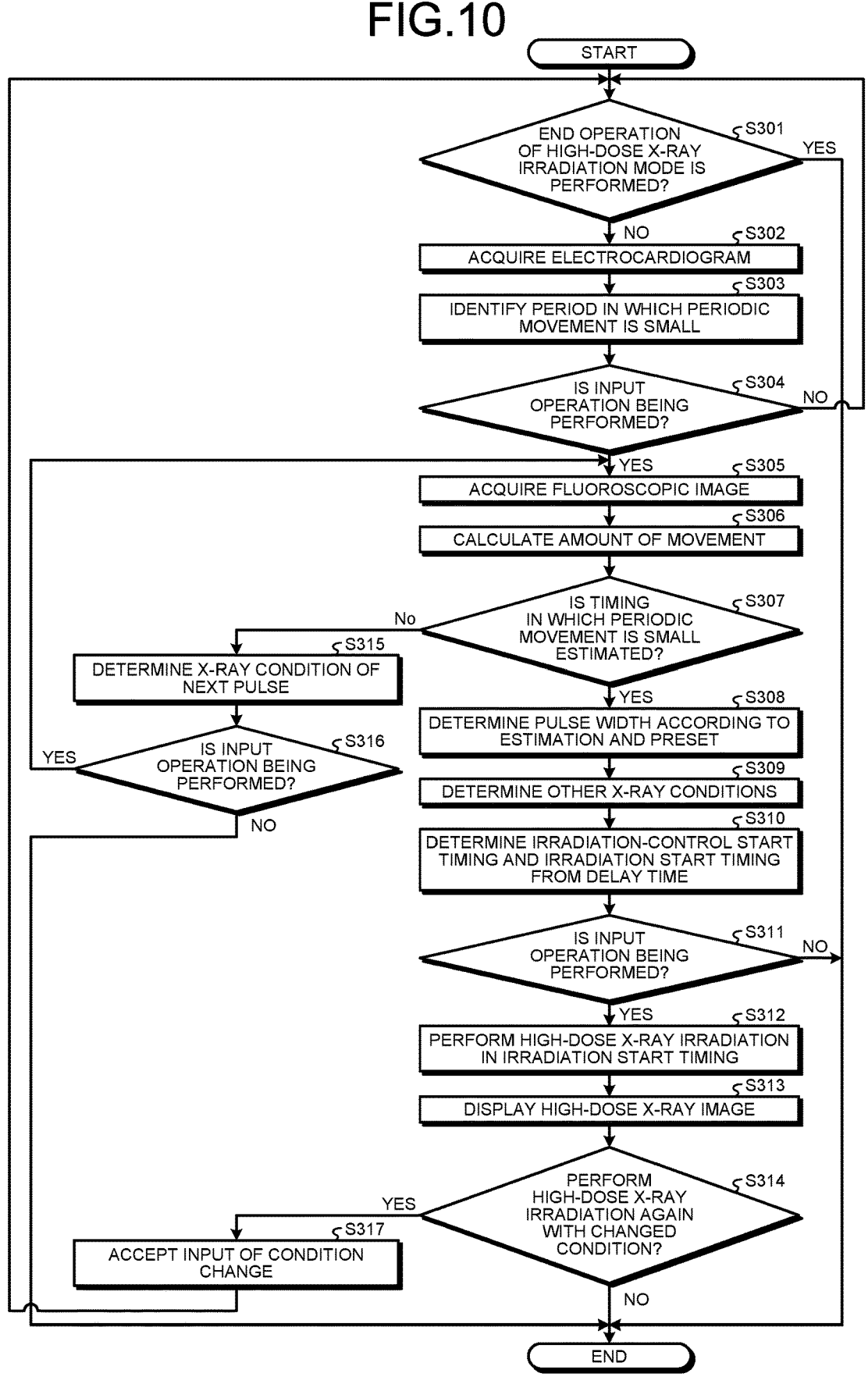
FIG. 10 is a flowchart illustrating a procedure of processing performed by an X-ray diagnostic apparatus according to the third embodiment.

First, a procedure of processing performed by the X-ray diagnostic apparatus according to the third embodiment will be explained. FIG. 10 is a flowchart illustrating the procedure of processing performed by the X-ray diagnostic apparatus 1 according to the third embodiment. The flowchart in FIG. 10 shows a case in which electrocardiogram data has been acquired prior to an input operation. In the procedure of processing illustrated in FIG. 10, an example in which the processing is ended when it is determined that and input operation is not being performed in determination whether an input operation is being performed by an operator, but it may be configured to return the processing flow to a start point when it is determined that an input operation is not being performed in the determination described above.

Steps S301 in FIG. 10 is implemented by the processing circuitry 21 reading and executing a program corresponding to the irradiation control function 213 from the storage circuitry 24. Step S302 is implemented by the acquiring circuitry 30 reading and executing a corresponding program from the storage circuitry 24. Furthermore, step S303 is implemented by the processing circuitry 21 reading and executing a program corresponding to the identifying function 211 from the storage circuitry 24. Moreover, Step S304 is implemented by the processing circuitry 21 reading and executing a program corresponding to the irradiation control function 213 from the storage circuitry 24. Moreover, step S305 is implemented by the processing circuitry 21 reading and executing a program corresponding to the irradiation control function 213 and the image-data generating function 214 from the storage circuitry 24. Furthermore, step S306 is implemented by the processing circuitry 21 reading and executing a program corresponding to the identifying function 211 and the image processing function 215 from the storage circuitry 24.

Moreover, step S307 is implemented by the processing circuitry 21 reading and executing a corresponding program to the identifying function 211 from the storage circuitry 24. Furthermore, step S308 to step S309 are implemented by the processing circuitry 21 reading and executing a program corresponding to the determining function 212 from the storage circuitry 24. Moreover, step S310 to step S312 are implemented by the processing circuitry 21 reading and executing a program corresponding to the irradiation control function 213 from the storage circuitry 24.

Furthermore, step S313 is implemented by the processing circuitry 21 reading and executing a program corresponding to the display control function 217, the image-data generating function 214, and the image processing function 215 from the storage circuitry 24. Moreover, step S314, step S317 are implemented by the processing circuitry 21 reading and executing a program corresponding to the irradiation control function 213 from the storage circuitry 24. Furthermore, step S315 is implemented by the processing circuitry 21 reading and executing a program corresponding to the determining function 212 from the storage circuitry 24. Moreover, step S316 is implemented by the processing circuitry 21 reading and executing a program corresponding to the irradiation control function 213 from the storage circuitry 24.

As illustrated in FIG. 10, in the X-ray diagnostic apparatus 1 according to the third embodiment, the processing circuitry 21 determines whether the end operation of the high-dose-X-ray irradiation mode has been performed (step S301). When the end operation has been performed (step S301: YES), the X-ray diagnostic apparatus 1 ends the processing. On the other hand, when the end operation of the high-dose X-ray irradiation mode has not been performed (step S301: NO), the acquiring circuitry 30 acquires electrocardiogram data (step S302). The processing circuitry 21 then identifies next timing of the period in which movement is relatively small based on the electrocardiogram data (step S303). When the input interface 22 accepts an input operation, the processing circuitry 21 determines whether the input operation is being continued (step S304). When the input operation is not being continued (step S304: NO), the processing circuitry 21 returns to step S301, and continues to determine whether a continuous input operation is accepted.

On the other hand, when the input operation is being continued (step S304: YES), the processing circuitry 21 acquires a fluoroscopic image, similarly to the X-ray diagnostic apparatus 1 according to the second embodiment (step S305). The processing circuitry 21 calculates an amount of movement of respective positions of the fluoroscopic image, and a cycle of movement (step S306).

The processing circuitry 21 estimates next timing of the period in which periodic movement is small by using a period based on the electrocardiogram identified at step S303 and a period based on the fluoroscopic image (step S307). Specifically, the processing circuitry 21 estimates next timing of the period in which periodic movement is small based on the period based on the electrocardiogram, the period based on the fluoroscopic image, and the delay time that is necessary until an electrocardiogram is transferred to the acquiring circuitry 30 from when the electrocardiogram is acquired by the electrocardiograph 2.

When the timing of the period in which periodic movement is small cannot be estimated (step S307: NO), a condition of an X-ray to be irradiated at step S312 described later will be changed from a value input in advance (preset) by the input interface 22 (step S315). The processing circuitry 21 then determines whether the input operation is being performed (step S316), and when the input operation is being performed (step S316: YES), returns to step S305 to acquire a fluoroscopic image. On the other hand, when the input operation is not being performed (step S316: NO), the processing circuitry 21 ends the processing.

On the other hand, when timing of the period in which periodic movement is small can be estimated (step S307: YES), the processing circuitry 21 determines a pulse width of an X-ray to be irradiated at step S312 described later according to the estimated period in which periodic movement is small and the X-ray condition (preset) input in advance by the input interface (step S308). Furthermore, the processing circuitry 21 determines X-ray conditions other than the pulse width (step S309).

Subsequently, the processing circuitry 21 determines irradiation-control start timing and irradiation start timing based on delay time that is necessary until an X-ray is actually irradiated from when an irradiation control signal of an X-ray is output (step S310). The processing circuitry 21 determines whether an input operation is being performed (step S311), and when an input operation is not being performed (step S311: NO), ends the processing. On the other hand, when an input operation is being performed (step S311: YES), the processing circuitry 21 controls the imaging device 10 according to the irradiation start timing, and performs high-dose X-ray irradiation (step S312).

The processing circuitry 21 generates an X-ray image of a relatively high dose by using a detection signal that is detected by irradiating an X-ray of a relatively high dose, and displays the generated high-dose X-ray image on the display 23 (step S313).

Subsequently, the processing circuitry 21 determines whether an input to perform high-dose X-ray irradiation again by changing a condition has been accepted, similarly to the X-ray diagnostic apparatus 1 according to the first embodiment (step S314). When the input to perform high-dose X-ray irradiation with a changed condition has been accepted (step S314: YES), the processing circuitry 21 accepts an input to change a condition (step S317), and returns to step S301 to perform the processing. On the other hand, when an input to perform high-dose X-ray irradiation with a changed condition is not accepted (step S314: NO), the processing circuitry 21 ends the processing.

Identification of Timing in which Periodic Movement is Small

As described above, at step S307, the identifying function 211 according to the third embodiment identifies a period in which movement is relatively small based on plural fluoroscopic images and electrocardiogram data. Specifically, the identifying function 211 identifies the period in which movement is relatively small based on a result of comparison by comparing the period in which movement is relatively small based on the fluoroscopic images and the period in which movement is relatively small based on the electrocardiogram data.

For example, the identifying function 211 identifies the period in which movement is relatively small based on a result of comparison by comparing the period based on the fluoroscopic images and the period based on the electrocardiogram data based on information about times at which the fluoroscopic images are collected and timestamp data of acquisition of the electrocardiogram data.

The identifying function 211 gives a priority to the period in which movement is relatively small based on the fluoroscopic images. That is, the identifying function 211 prioritizes the period based on an amount of movement actually calculated. For example, the identifying function 211 identifies the period based on the fluoroscopic images as the period in which movement is relatively small, when the period based on the fluoroscopic images and the period based on the electrocardiogram are identified as respective different periods, when the period based on the fluoroscopic images and the period based on the electrocardiogram are identified as periods partially overlap each other, and when the period based on the fluoroscopic images is identified as a period included in the period based on the electrocardiogram.

On the other hand, when the period based on the electrocardiogram is identified as a period included in the period based on the fluoroscopic images, the identifying function 211 may identify the period based on the fluoroscopic images as the period in which movement is relatively small, or may identify the period based on the electrocardiogram as the period in which movement is relatively small.

Moreover, when identification of the period based on the fluoroscopic images has failed, the identifying function 211 can identify the period based on the electrocardiogram as the period in which movement is relatively small. When identification of the period based on the fluoroscopic images fails includes a case in which, for example, when fluoroscopic images corresponding to three heartbeats are acquired, and an amount of movement is calculated, timing in which the amount of movement becomes lower than the threshold varies per heartbeat, and the like.

The determining function 212 determines a pulse width and other X-ray conditions based on the period in which movement is relatively small identified by the identifying function 211. The irradiation control function 213 determines irradiation start timing by arranging a pulse of the pulse width determined by the determining function 212 in the period in which movement is relatively small. Furthermore, the irradiation control function 213 determines a point of time preceding from the irradiation start timing by the delay time that is necessary until an X-ray is actually irradiated from when the irradiation control signal of an X-ray is output (for example time t1 in FIG. 6), as the irradiation-control start timing.

As described above, according to the third embodiment, the identifying function 211 identifies a period in which periodic movement is small based on plural fluoroscopic images and electrocardiogram data. Therefore, the X-ray diagnostic apparatus 1 according to the third embodiment can identify a period in which periodic movement is small by multiple methods, and enables processing to proceed without affecting following processing even if it is failed with one method.

Fourth Embodiment

Figure 11:
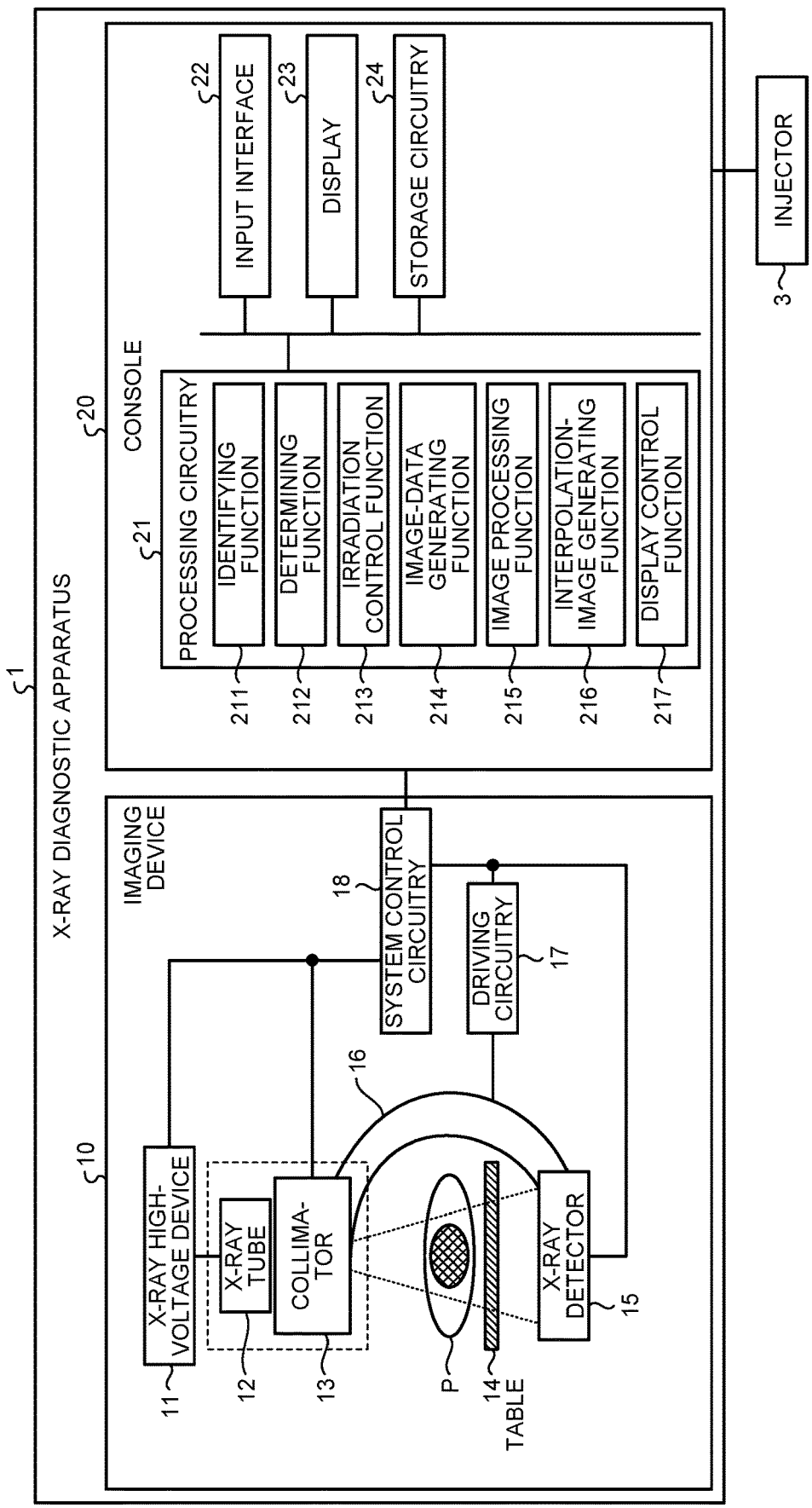
FIG. 11 is a block diagram illustrating an example of a configuration of an X-ray diagnostic apparatus according to a fourth embodiment.

In the first to the third embodiments described above, a case in which high-dose X-ray irradiation is performed in a period in which periodic movement is small, and a high-dose X-ray image is generated to be displayed has been explained. In the fourth embodiment, a case in which high-dose X-ray irradiation is performed, linked further with contrast-agent injection timing. FIG. 11 is a block diagram illustrating an example of a configuration of the X-ray diagnostic apparatus 1 according to a fourth embodiment. The X-ray diagnostic apparatus 1 according to the fourth embodiment differs in a point in which an injector 3 is connected to the X-ray diagnostic apparatus 1, and processing performed by the identifying function 211, the irradiation control function 213, the image processing function 215, and the interpolation-image generating function 216 from the X-ray diagnostic apparatus 1 according to the first embodiment. In the following, these points are mainly explained.

The injector 3 is a device to inject a contrast agent from a catheter inserted in the subject P. The contrast agent injection from the injector 3 is performed according to an injection instruction received through the processing circuitry 21. Specifically, the injector 3 performs contrast agent injection according to a contrast-agent injection condition including an injection start instruction of a contrast agent, an injection stop instruction, and an injection speed, received from the processing circuitry 21. The injector 3 can perform injection start and injection stop according to the injection instruction input directly to the injector 3 by an operator also.

The identifying function 211 according to the fourth embodiment identifies a period in which periodic movement is small in the subject in which a contrast agent is injected. Specifically, the identifying function 211 identifies a period in which periodic movement is small after the contrast agent has reached a region of interest. For example, the identifying function 211 identifies next timing of a period in which periodic movement is small based on at least one of plural X-ray images and electrocardiogram data, thereby identifying occurrence cycle of the period as explained in the first to the third embodiments. That is, the identifying function 211 identifies chronological occurrence timing of the period in which periodic movement is small.

The identifying function 211 identifies the period in which periodic movement is small after the contrast agent reaches a region of interest based on a contrast state in the region of interest of the subject. For example, the identifying function 211 identifies occurrence timing of the period in which periodic movement is small after the contrast agent reaches the region of interest in the chronological occurrence timing of the period in which periodic movement is small.

The identifying function 211 can identify the period in which periodic movement is small occurring after the contrast agent reaches the region of interest based on the contrast state in the region of agent, while identifying next timing of the period in which periodic movement is small all the time based on at least one of the X-ray images and the electrocardiogram data.

The irradiation control function 213 according to the fourth embodiment determines irradiation start timing according to an injection state of a contrast agent into a blood vessel. Specifically, the irradiation control function 213 determines irradiation start timing to perform high-dose X-ray irradiation in a period in which periodic movement is small occurring after the contrast agent reaches a region of interest. For example, the irradiation control function 213 determines irradiation-control start timing and irradiation start timing by using various kinds of delay time, similarly to the first to the third embodiments.

In the following, an example of high-dose X-ray irradiation according to the contrast state of the region of interest will be explained. For example, the X-ray diagnostic apparatus 1 according to the fourth embodiment performs high-dose X-ray irradiation linked with the contrast-agent injection timing by using elapsed time from a start of contrast agent injection.

In such a case, the identifying function 211 identifies a period in which periodic movement is small after set time has passed since injection of the contrast agent into a blood vessel is started. Setting of elapsed time is performed in advance, for example, based on a distance from an injection position of a contrast agent to a region of interest, an injection speed of a contrast agent, and the like. That is, based on time necessary for a contrast agent to reach a region of interest, elapsed time is set.

The irradiation control function 213 determines irradiation start timing in the period in which periodic movement is small after the elapsed time from the start of contrast agent injection has passed, and performs high-dose X-ray irradiation. Thus, the X-ray diagnostic apparatus 1 according to the fourth embodiment can collect high-dose X-ray images in which blurriness is few in a state in which the contrast agent has reached the region of interest. For example, by performing the above processing at a position at which a stent is indwelled as the region of interest, an X-ray image enabling to observe a degree of adhesion of a blood vessel wall and the stent can be obtained.

Moreover, as for high-dose X-ray irradiation according to a contrast state of a region of interest, for example, the X-ray diagnostic apparatus 1 according to the fourth embodiment determines the contrast state of the region of interest based on a contrasted image, and performs high-dose X-ray irradiation linked with the contrast-agent injection timing by using a determination result. For example, the identifying function 211 determines a contrast state in a region of interest from a contrasted image collected after injection of a contrast agent, and identifies a period in which periodic movement is small. As one example, the identifying function 211 sequentially extracts plural contrasted images that are sequentially collected after injection of a contrast agent. The identifying function 211 identifies the period in which periodic movement is small after timing in which the extracted contrast agent area exceeds a predetermined area. That is, the identifying function 211 regards the timing in which the contrast agent area exceeds the predetermined area as timing in which the contrast agent has reached the region of interest, and identifies the period in which periodic movement is small after the timing in which the contrast agent has reached the region of interest.

The identifying function 211 can extract the contrast agent area in the contrasted image by using a method based on a brightness value in the contrasted image, or a method such as deep learning.

The irradiation control function 213 determines irradiation start timing in the period in which periodic movement is small identified based on an area of the contrast agent area in the contrasted image, and performs high-dose X-ray irradiation. In this method also, similarly to the method using the elapsed time, the X-ray diagnostic apparatus 1 can collect high-dose X-ray images in which blurriness is few in a state in which the contrast agent has reached the region of interest.

When the set elapsed time and time until the contrast agent area exceeds the predetermined area are shorter than time that is necessary for identifying the period in which periodic movement is small based on at least one of plural X-ray images and electrocardiogram data, the irradiation control function 213 controls to perform high-dose X-ray irradiation in the period in which periodic movement is small identified by the identifying function 211 as explained in the first to the third embodiments.

As described above, the X-ray diagnostic apparatus 1 according to the fourth embodiment can perform high-dose X-ray irradiation, linked with the contrast-agent injection timing of a contrasted image. For example, in collection of a contrasted image by digital angiography (DA), contrasted images before and after high-dose X-ray irradiation can also be stored at the same time.

Therefore, the irradiation control function 213 according to the fourth embodiment can control to sequentially generate X-ray images by irradiating an X-ray at a lower dose than a dose in X-ray irradiation after performing the X-ray irradiation of a relatively high dose. That is, the irradiation control function 213 can control such that collection of contrasted image at a predetermined dose (hereinafter, also denoted as normal dose irradiation) is started, and after performing high-dose X-ray irradiation in a period in which periodic movement is small, collection of contrasted images at an original dose is continued to be performed. For example, the X-ray diagnostic apparatus 1 has a mode of collecting contrasted images described above, and performs collection of contrasted image described above according to mode switch made through the input interface 22.

The display control function 217 can display a series stored in collection of contrasted images described above in a moving image on the display 23. In one series of contrasted images, only one frame among high-dose X-ray images collected by high-dose X-ray irradiation has a significantly good image quality. The display control function 217 can display the moving image in which only one frame has a good image quality out of the high-dose X-ray images, but can also improve smoothness at the time of checking the moving image by displaying a high-dose X-ray image, an image quality of which is reduced.

In such a case, the image processing function 215 according to the fourth embodiment generates a high-dose X-ray image by subjecting a high-dose X-ray image to degradation processing. The degradation processing is processing to correct a difference in image quality originated in different doses in the X-ray detector 15, the X-ray tube 12, and the collimator 13. The image processing function 215 reduces an image quality of a high-dose X-ray image so as to obtain an image quality equivalent to previous and following frames by performing the correction described above with respect to the high-dose X-ray image.

The display control function 217 displays the moving image in which the high-dose X-ray image in one series of the contrasted images with the generated high-dose X-ray image subject to the degradation processing on the display 23.

Moreover, one series of the contrasted images described above are ones collected by performing normal dose irradiation and high-dose X-ray irradiation. Therefore, when time is necessary for switching between the normal dose irradiation and the high-dose X-ray irradiation, a gap can be created between a frame collected by the normal dose irradiation and a frame collected by the high-dose X-ray irradiation, and smoothness in moving image checking can be deteriorated.

Therefore, the display control function 217 displays a moving image in which an interpolation image is inserted between the frame collected by the normal dose irradiation and the frame collected by the high-dose X-ray irradiation. In such a case, the interpolation-image generating function 216 generates an interpolation image corresponding to a time phase between the frame collected by the normal dose irradiation and the frame collected by the high-dose X-ray irradiation.

The interpolation-image generating function 216 generates an interpolation image corresponding to a time phase between a time phase of a contrasted image acquired last for plural contrasted images and a time phase of a high-dose X-ray image acquired by high-dose X-ray irradiation. Moreover, the interpolation-image generating function 216 generates an interpolation image corresponding to a time phase between a time phase of the high-dose X-ray image and a time phase of a contrasted image acquired by performing X-ray irradiation at a lower dose than a dose in the X-ray irradiation after performing high-dose X-ray irradiation. That is, the interpolation-image generating function 216 generates respective interpolation images corresponding to time phases before and after performing high-dose X-ray irradiation.

For example, the interpolation-image generating function 216 estimates a contrast state corresponding to a time phase between a time phase before performing high-dose X-ray irradiation and a time phase in which the high-dose X-ray irradiation is performed from the contrast state of the last frame before performing the high-dose X-ray irradiation and the contrast state in the high-dose X-ray image, and generates an interpolation image showing the estimated contrast state. Moreover, for example, the interpolation-image generating function 216 estimates a contrast state corresponding to a time phase between a time phase after high-dose X-ray irradiation is performed and a time phase in which the high-dose X-ray irradiation is performed from the contrast state of the first frame after the high-dose X-ray irradiation is performed and the contrast state in the high-dose X-ray image, and generates an interpolation image showing the estimated contrast state.

The display control function 217 displays a moving image in which the interpolation image generated by the interpolation-image generating function 216 is inserted in one series of the contrasted images described above. The display control function 217 can display image indicating that an interpolation image is inserted in a moving image, or information indicating which frame is the interpolation image.

In the fourth embodiment described above, the processing circuitry 21, the driving circuitry 17, the system control circuitry 18 can be regarded as one unit, and this can be understood as "processing circuitry".

As described above, according to the fourth embodiment, the irradiation control function 213 determines irradiation start timing according to an injection state of a contrast agent into a blood vessel. Therefore, the X-ray diagnostic apparatus 1 according to the fourth embodiment enables to perform high-does X-ray irradiation linked with contrast-agent injection timing.

Furthermore, according to the fourth embodiment, the identifying function 211 identifies a period in which periodic movement is small after predetermined time has passed since injection of a contrast agent into a blood vessel is started. The irradiation control function 213 determines irradiation start timing based on the identified period in which periodic movement is small. Accordingly, the X-ray diagnostic apparatus 1 according to the fourth embodiment enables to perform high-dose X-ray irradiation linked with contrast-agent injection timing easily.

Moreover, according to the fourth embodiment, the irradiation control function 213 determines an injection state of a contrast agent into a blood vessel based on plural X-ray images, and determines irradiation start timing according to a determination result. Therefore, the X-ray diagnostic apparatus 1 according to the fourth embodiment enables to perform high-dose X-ray irradiation at high accuracy in a state in which a region of interest is contrasted.

Furthermore, according to the fourth embodiment, the irradiation control function 213 controls to irradiate an X-ray at a lower dose than a dose in X-ray irradiation after the X-ray irradiation of a relatively high dose is performed, to sequentially generate X-ray images. Therefore, the X-ray diagnostic apparatus 1 according to the fourth embodiment enables to collect a high-dose X-ray image and one series of X-ray image group including X-ray images before and after the high-dose X-ray image chronologically.

Moreover, according to the fourth embodiment, the image processing function 215 performs degradation processing with respect to the high-dose X-ray image acquired by performing X-ray irradiation of a relatively high dose. Therefore, the X-ray diagnostic apparatus 1 according to the fourth embodiment enables to improve visibility when a high-dose X-ray image collected by high-dose X-ray irradiation and an X-ray image collected by normal dose irradiation are consecutively displayed.

Furthermore, according to the fourth embodiment, the interpolation-image generating function 216 generates an interpolation image corresponding to a time phase between a time phase of an X-ray image acquired last for plural X-ray images and a time phase of a high-dose X-ray image acquired by performing X-ray irradiation of a relatively high dose. Therefore, the X-ray diagnostic apparatus 1 according to the fourth embodiment enables to improve visibility of a moving image even when time is necessary for switching from the normal dose irradiation to the high-dose X-ray irradiation.

Moreover, according to the fourth embodiment, the interpolation-image generating function 216 generates an interpolation image corresponding to a time phase between a time phase of a high-dose X-ray image and a time phase of an X-ray image that is acquired by irradiating an X-ray at a lower dose than a dose in X-ray irradiation after the X-ray irradiation of a relatively high dose is performed. Therefore, the X-ray diagnostic apparatus 1 according to the fourth embodiment enables to improve visibility of a moving image even when time is necessary for switching from the high-dose X-ray irradiation to the normal dose irradiation.

Furthermore, according to the fourth embodiment, the display control function 217 sequentially displays plural X-ray images, an interpolation image corresponding to a time phase between a time phase of an X-ray image acquired last in plural X-ray images and a time phase of a high-dose X-ray image, and the high-dose X-ray image on a display. Therefore, the X-ray diagnostic apparatus 1 according to the fourth embodiment enables to present a moving image, the visibility of which is improved even when time is necessary for switching from the normal dose irradiation to the high-dose X-ray irradiation.

Other Embodiments

The first to the fourth embodiments have so far been explained, but embodiments may be performed in various forms other than the first to the fourth embodiments described above.

In the above embodiment, a case in which an amount of movement is calculated by performing inter-frame difference or optical flow with respect to fluoroscopic images, which are X-ray images of plural frames sequentially collected, as a method of calculating the amount of movement by the image processing function 215 has been explained. However, embodiments are not limited thereto, and when a device on which markers are attached is rendered in a fluoroscopic image, the image processing function 215 may calculate an amount of movement by detecting the marker pair as feature points.

Moreover, when a device is an object to be observed, by detecting the device by using a marker pair or the like as pre-calculation processing for an amount of movement in an X-ray image, and by performing segmentation, the identifying function 211 can process only an image region including the device obtained by segmentation as a subject for which an amount of movement is calculated. That is, by calculating an amount of movement for the segmented image region by the image processing function 215, the identifying function 211 can reduce calculation time for an amount of movement. Because a next time phase in which a period in which movement is relatively small occurs is identified by observing fluctuation by heartbeats of a subject in real time through a fluoroscopic image, reduction of calculation time of an amount of movement reduces time necessary for identifying the period in which movement is relatively small. By identifying the period in which movement is relatively small in short time, time to be elapsed since fluoroscopy is performed can be reduced, and the period in which movement is relatively small can be identified with high accuracy.

In the embodiment describe above, a case in which an ordinary detector is used as the X-ray detector 15 has been explained. However, embodiments are not limited thereto, and a detector that is capable of non-destructive and multiple readouts may be used. Non-destructive and multiple readouts is to perform reading of a signal value plural times during one pulse of X-ray irradiation. In the following, a detector that is capable of non-destructive and multiple readouts will be explained with an example in which reading is performed five times during one pulse of X-ray irradiation.

In such a case, when a period in which reading is to be performed is one frame, the number of frames included within one pulse is five. A readout value of each frame is a signal value accumulated from when X-ray irradiation of one pulse is started. The readout value of a target frame is calculated from a difference from a readout value of a previous frame.

Figure 12:
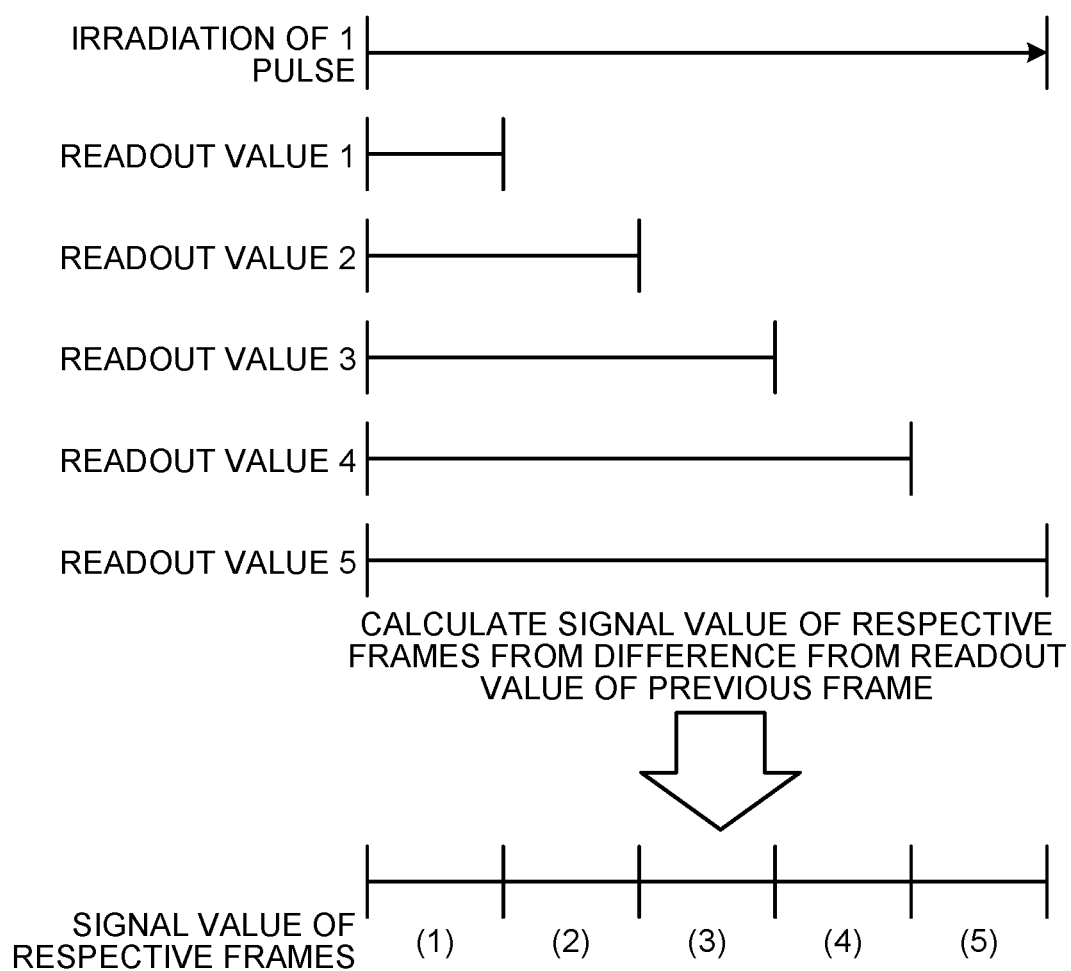
FIG. 12 is a diagram for explaining an example of a detector that is capable of non-destructive and multiple readouts according to another embodiment.

FIG. 12 is a diagram for explaining an example of a detector that is capable of non-destructive and multiple readouts according to another embodiment. In FIG. 12, a case in which five frames are generated from X-ray irradiation of one pulse by performing five times of readout in irradiation of one pulse is illustrated. For example, in FIG. 12, a read out value of a signal value (1) of the first frame is 1, and is a signal value accumulated since a start of irradiation. A detector that is capable of non-destructive and multiple readout accumulates a signal value without canceling an accumulated signal value even when a signal value of the first frame is readout. That is, a readout value 2 readout next is a value in which a signal is further accumulated to the readout value 1.

Therefore, a signal value (2) of the second frame is a value calculated by subtracting the readout value 1 from the readout value 2. Similarly, signal values of the third to the fifth frames are calculated by subtracting a previous readout value from a readout value. By using such a detector, an amount of movement can be calculated by irradiation of one pulse. As a result, for example, even when a fluoroscopic image is collected at a frame rate lower than that in a normal case, an amount of movement can be calculated. Moreover, for example, also when a fluoroscopic image is collected at a frame rate higher than that in a normal case, an amount of movement can be calculated more accurately than a case in which an amount of movement is calculated using the fluoroscopic image.

The identifying function 211 according to the other embodiment calculates a degree of periodic movement based on plural X-ray images based on multiple times of readout results by the detector that performs multiple readouts while one pulse of an X-ray is irradiated. Therefore, the X-ray diagnostic apparatus 1 according to the other embodiment can calculate an amount of movement in one pulse, and enables to improve the accuracy in identifying the period in which periodic movement is small.

Moreover, in the first embodiment described above, a case in which an interpolation image corresponding to a time phase between a time phase of the last frame in plural fluoroscopic images and a time phase of a frame (high-dose X-ray image) collected by performing high-dose X-ray irradiation has been explained. However, embodiments are not limited thereto, and for example, after a high-dose X-ray image is collected, a fluoroscopic frame may be collected again.

Furthermore, in this case, an interpolation image corresponding to a time phase between a time phase of the frame collected by performing high-dose X-ray irradiation and a time phase of a frame at a start of fluoroscopy performed again may be generated.

In such a case, the display control function 217 can control to display a moving image in which respective frames collected by fluoroscopy, a high-dose X-ray image, and an interpolation image are used.

Moreover, the display control function 217 can control to display a moving image in which respective frames collected by fluoroscopy, and a high-dose X-ray image subjected to the degradation processing are used.

In The X-ray diagnostic apparatus explained in the respective embodiments, respective processing functions are stored in the storage circuitry 24 in a form of a computer executable program. The processing circuitry 21 is a processor that implements a function corresponding to respective programs by reading and executing the programs from the storage circuitry 24. In other words, the processing circuitry 21 that has read a program from the storage circuitry 24 is to have a function corresponding to a program read out. In the respective embodiments described above, a case in which the respective processing functions are implemented by a single unit of the processing circuitry 21, but embodiments are not limited thereto. For example, the processing circuitry 21 may be constituted by combining plural independent processors, and may be configured to implement the respective processing functions by the respective processors executing the respective programs. Moreover, the respective processing functions included in the processing circuitry 21 may be implemented by a single unit of or plural units of the processing circuits in a distributed or integrated manner appropriately.

A term "processor" used in the above explanation signifies a circuit, such as a central processing unit (CPU), a graphical processing unit (GPU), an application specific integrated circuit (ASIC), a programmable logic device (for example, simple programmable logic device (SPLD), complex programmable logic device (CPLD)), and a field programmable gate array (FPGA). The processor implements a function by reading and executing a program stored in a storage 111.

In the respective embodiments described above, it has been explained that the storage circuitry 24 stores programs corresponding to the respective functions. However, plural units of the storage circuitry 24 may be arranged in a distributed manner, and the processing circuitry 21 may be configured to read a corresponding program from an individual unit of the storage circuitry 24. Moreover, instead of storing a program in the storage circuitry 24, it may be configured to directly install a program in a circuit of the processor. In this case, the processor reads and executes the program installed in the circuit, to implement the function.

The respective components of the respective devices according to the embodiments described above are of functional concept, and it is not necessarily required to be configured physically as illustrated. That is, specific forms of distribution and integration of the respective devices are not limited to the ones illustrated, and all or some thereof can be configured to be distributed or integrated functionally or physically in arbitrary units according to various kinds of loads, usage conditions, and the like. Furthermore, as for the respective processing functions performed by the respective devices, all or an arbitrary part thereof can be implemented by a CPU and a computer program that is analyzed and executed by the CPU, or can be implemented as hardware by wired logic.

Moreover, the control method explained in the above embodiments can be implemented by executing a program that has been prepared in advance by a computer such as a personal computer and a workstation. This control program can be distributed through a network such as the Internet. Furthermore, this control program can be recorded on a non-transient recording medium, such as a hard disk, a flexible disk (FD), a compact-disk read-only memory (CD-ROM), a magneto optical disk (MO), and a digital versatile disk (DVD), and can be executed by being read by a computer from the recording medium.

According to at least one of the embodiments explained above, observation of a device can be facilitated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an input interface configured to accept an input operation performed by an operator; and
processing circuitry configured to
identify a period in which periodic movement is small in an irradiation area of an X-ray,
determine irradiation start timing of an X-ray according to the period, and
control to perform X-ray irradiation of a relatively high dose in the determined irradiation start timing on condition that the input operation is being continued.

2. The X-ray diagnostic apparatus according to claim 1, wherein the processing circuitry is configured to
sequentially generate X-ray images based on an X-ray that has been emitted from an X-ray tube, and that has passed through a subject, and
identify the period in which periodic movement is small based on a plurality of X-ray images sequentially generated.

3. The X-ray diagnostic apparatus according to claim 1, wherein the processing circuitry is configured to identify the period in which periodic movement is small based on electrocardiogram data.

4. The X-ray diagnostic apparatus according to claim 2, wherein the processing circuitry is configured to identify the period in which periodic movement is small based on the X-ray images and electrocardiogram data.

5. The X-ray diagnostic apparatus according to claim 1, wherein the processing circuitry is configured to determine an X-ray condition based on the period in which periodic movement is small according to continuation of the input operation.

6. The X-ray diagnostic apparatus according to claim 5, wherein the processing circuitry is configured to determine a pulse width according to length of the period in which periodic movement is small.

7. The X-ray diagnostic apparatus according to claim 5, wherein the processing circuitry is configured to determine a focal spot size according to length of the period in which periodic movement is small and a targeted dose.

8. The X-ray diagnostic apparatus according to claim 2, wherein the processing circuitry is configured to calculate, based on the X-ray images, a degree of the periodic movement at respective positions in the X-ray images.

9. The X-ray diagnostic apparatus according to claim 2, wherein the processing circuitry is configured to calculate a degree of movement based on a magnitude of the periodic movement at respective positions in the X-ray images and a weighting coefficient corresponding to the respective positions.

10. The X-ray diagnostic apparatus according to claim 2, wherein the processing circuitry is configured to determine, according to continuation of the input operation, a pulse width for the X-ray irradiation of a relatively high dose, based on a pulse width for X-ray irradiation at generating the X-ray images and motion blur in the X-ray images.

11. The X-ray diagnostic apparatus according to claim 1, further comprising
a detector configured to perform a plurality of readouts during irradiation of an X-ray for one pulse, wherein
the processing circuitry is configured to calculate a degree of the periodic movement by using a plurality of X-ray images based on a result of the readouts by the detector.

12. The X-ray diagnostic apparatus according to claim 1, wherein the processing circuitry is configured to determine the irradiation start timing according to an injection state of a contrast agent into a blood vessel.

13. The X-ray diagnostic apparatus according to claim 1, wherein the processing circuitry is configured to
identify the period in which periodic movement is small after set time has passed since injection of a contrast agent into a blood vessel is started, and
determine the irradiation start timing based on the identified period in which periodic movement is small.

14. The X-ray diagnostic apparatus according to claim 1 wherein the processing circuitry is configured to
determine an injection state of a contrast agent based on a plurality of X-ray images collected at injection of the contrast agent into a blood vessel, and
determine the irradiation start timing according to a determination result.

15. The X-ray diagnostic apparatus according to claim 2, wherein the processing circuitry is configured to control to irradiate, after the X-ray irradiation of a relatively high dose is performed, an X-ray at a lower dose than a dose in the X-ray irradiation, and to sequentially generate X-ray images.

16. The X-ray diagnostic apparatus according to claim 2, wherein the processing circuitry is configured to subject a high-dose X-ray image that is acquired by the X-ray irradiation of a relatively high dose to degradation processing.

17. The X-ray diagnostic apparatus according to claim 2, wherein the processing circuitry is configured to generate an interpolation image corresponding to a time phase between a time phase of an X-ray image that is acquired last in the X-ray images, and a time phase of a high-dose X-ray image acquired by the X-ray irradiation of a relatively high dose.

18. The X-ray diagnostic apparatus according to claim 17, wherein the processing circuitry is configured to generate an interpolation image corresponding to a time phase between a time phase of the high-dose X-ray image, and a time phase of an X-ray image acquired by irradiating, after performing the X-ray irradiation of a relatively high dose, an X-ray at a lower dose than a dose in the X-ray irradiation.

19. The X-ray diagnostic apparatus according to claim 1, wherein the processing circuitry is configured to determine the irradiation start timing according to time necessary until the X-ray irradiation is performed from when a control signal to instruct the X-ray irradiation of a relatively high dose is output.

20. The X-ray diagnostic apparatus according to claim 3, wherein the processing circuitry is configured to
acquire electrocardiogram data from an electrocardiograph, and
determine the irradiation start timing according to time from a signal is output by the electrocardiograph until the signal is acquired.

21. The X-ray diagnostic apparatus according to claim 1, wherein the input interface is configured to accept an input operation to switch an irradiation mode in which the X-ray irradiation of a relatively high dose is performed, before accepting continuation of an input operation.

22. The X-ray diagnostic apparatus according to claim 1, wherein
the input interface is configured to accept a change input operation made by an operator relating to at least one of the irradiation start timing and an X-ray condition, according to a state of a high-dose X-ray image that is acquired by X-ray irradiation of a relatively high dose, and
the processing circuitry is configured to control to perform the X-ray irradiation of a relatively high dose in which at least one of the irradiation start timing and the X-ray condition is changed, according to the change input operation.

23. The X-ray diagnostic apparatus according to claim 1, wherein the processing circuitry is configured to cause a display to display a high-dose X-ray image that is acquired by the X-ray irradiation of a relatively high dose.

24. The X-ray diagnostic apparatus according to claim 23, wherein the processing circuitry is configured to cause the display to sequentially display a plurality of X-ray images, an interpolation image corresponding to a time phase between a time phase of an X-ray image acquired last in the X-ray images and a time phase of the high-dose X-ray image, and the high-dose X-ray image.

* * * * *